(12) United States Patent
Stritch

(10) Patent No.: US 11,529,163 B2
(45) Date of Patent: Dec. 20, 2022

(54) SURGICAL SYSTEMS AND TOOLS FOR MOVING ENERGY APPLICATORS IN SUPERIMPOSED MODES

(71) Applicant: Stryker European Holdings I, LLC, Kalamazoo, MI (US)

(72) Inventor: Thomas Stritch, Newmarket (IE)

(73) Assignee: Stryker European Holdings I, LLC, Kalamazoo, MI (US)

( * ) Notice: Subject to any disclaimer, the term of this patent is extended or adjusted under 35 U.S.C. 154(b) by 913 days.

(21) Appl. No.: 16/372,498

(22) Filed: Apr. 2, 2019

(65) Prior Publication Data

US 2019/0298404 A1 Oct. 3, 2019

Related U.S. Application Data

(60) Provisional application No. 62/651,290, filed on Apr. 2, 2018.

(51) Int. Cl.
*A61B 17/32* (2006.01)
*A61B 17/3207* (2006.01)
(Continued)

(52) U.S. Cl.
CPC .... *A61B 17/320068* (2013.01); *A61B 17/142* (2016.11); *A61B 17/320758* (2013.01);
(Continued)

(58) Field of Classification Search
CPC .......... A61B 17/320068; A61B 17/142; A61B 2017/32098; A61B 2017/0075;
(Continued)

(56) References Cited

U.S. PATENT DOCUMENTS 3,471,724 A 10/1969 Balamuth
4,188,952 A 2/1980 Loschilov et al.
(Continued)

OTHER PUBLICATIONS

Aro, H. et al., "Ultrasonic Device in Bone Cutting: A Histological and Scanning Electron Microscopial Study", Acta Orthopaedica Scandivavica, vol. 52, No. 1, 2009, 7 pages.
(Continued)

*Primary Examiner* — Marcela I. Shirsat
(74) *Attorney, Agent, or Firm* — Howard & Howard Attorneys PLLC

(57) ABSTRACT

A surgical tool may move a saw blade in a sagittal plane. The saw blade has a distal blade end with teeth. The surgical tool comprises a handpiece body and a carrier operatively attached to the handpiece body. The carrier is configured for oscillating movement about a pivot axis. A retainer is operatively attached to the carrier for concurrent movement and releasably secures the saw blade in the sagittal plane relative to the handpiece body. An actuator is coupled to the handpiece body to selectively oscillate the carrier relative to the handpiece body such that the retainer and the saw blade pivot back and forth about the pivot axis within the sagittal plane. An ultrasonic transducer is operatively attached to the handpiece body to selectively generate ultrasonic energy to resonate the saw blade such that the teeth at the distal blade end reciprocate proximally and distally within the sagittal plane.

17 Claims, 27 Drawing Sheets

(51) Int. Cl.
*A61B 17/14* (2006.01)
*A61B 17/00* (2006.01)
*B23D 49/16* (2006.01)
*B23D 51/16* (2006.01)

(52) U.S. Cl.
CPC ............ *A61B 2017/00075* (2013.01); *A61B 2017/00106* (2013.01); *A61B 2017/00477* (2013.01); *A61B 2017/00924* (2013.01); *A61B 2017/320071* (2017.08); *A61B 2017/320074* (2017.08); *A61B 2017/320098* (2017.08); *B23D 49/162* (2013.01); *B23D 49/165* (2013.01); *B23D 51/16* (2013.01)

(58) Field of Classification Search
CPC ........... A61B 2017/00106; A61B 2017/00477; A61B 2017/320074; A61B 2017/00924; A61B 2017/320071; A61N 7/00; B23D 51/10; B23D 51/16; B23D 51/66; B23D 49/162; B23D 49/165; B27B 19/00; B27B 19/002; B27B 19/006
USPC .............................. 606/82; 30/390, 392–394
See application file for complete search history.

(56) References Cited

U.S. PATENT DOCUMENTS

| | | | |
|---|---|---|---|
| 4,920,946 | A | 5/1990 | Kuromatsu |
| 7,691,106 | B2 | 4/2010 | Schenberger et al. |
| 7,824,247 | B1 | 11/2010 | Bar-Cohen et al. |
| 8,531,064 | B2 | 9/2013 | Robertson et al. |
| 10,251,663 | B2 | 4/2019 | Behzadi |
| 2005/0262708 | A1* | 12/2005 | Haas ...................... B23D 51/16 30/392 |

OTHER PUBLICATIONS

Astashev, V.K. et al., "Ultrasonic Cutting as a Nonlinear (Vibro-Impact) Process", Ultrasonics, vol. 36, 1998, pp. 89-96.
Khambay, B.S. et al., "Abstract of Investigations Into the Use of an Ultrasonic Chisel to Cut Bone Part 2: Cutting Ability", J. Dent. vol. 28, No. 1, 2000, pp. 39-44.
Macbeath, Alan, "Ultrasonic Bone Cutting Thesis", University of Glasgow, Mar. 2006, 170 pages.
Richards, Daniel et al., "Ultrasonically Assisted Cuttng Blades for Large Bone Surgeries Presentation", University of Glasgow, 2017, 26 pages.
Richards, Daniel et al., "Ultrasonically Assisted Cuttng Blades for Large Bone Surgeries", Proceedings of Meetings on Acoustics, Honolulu, vol. 32, Dec. 18-20, 2017, 5 pages.
Sinn, G. et al., "Ultrasonic-Assisted Cutting of Wood", Journal of Materials Processing Technology, vol. 170, 2005, pp. 42-49.
Thampy, Anila et al., "A Smart Ultrasonic Cuttng System for Surgery", School of Engineering, Physics and Mathematics, University of Dundee, UK, IFMBE Proceedings, Vo., 22, 2008, pp. 907-910.
Wang, Yao-Hsien et al., "Quality and Throughput Improvement of GaN/SiC Wafer Sawing with the Addition of Ultrasonic Power", CS MANTECH Conference, Colorado, May 19-22, 2014, 4 pages.
Richards, Daniel et al., "An Ultrasonically Assisted Sagittal Saw for Large Bone Surgeries", IEEE International Ultrasonics Symposium, Oct. 21-24, 2015, 5 pages.
Shu, Liming et al., "Design and Experimental Force Analysis of a Novel Elliptical Vibration Assisted Orthopedic Oscillating Saw", Medical Engineering and Physics, vol. 54, 2018, pp. 22-31.
Richards, Daniel et al., An ultrasonically assisted sagittal saw for large bone surgeries; abstract only, 2015 IEEE International Ultrasonics Symposium, Oct. 21-24, 2015; 1 page.
Sugita, Naohiko et al., "Novel surgical machining via an impact cutting method based on fracture analysis with a discontinuum bone model", CIRP Annals—Manufacturing Technology (2017); 4 pages.

* cited by examiner

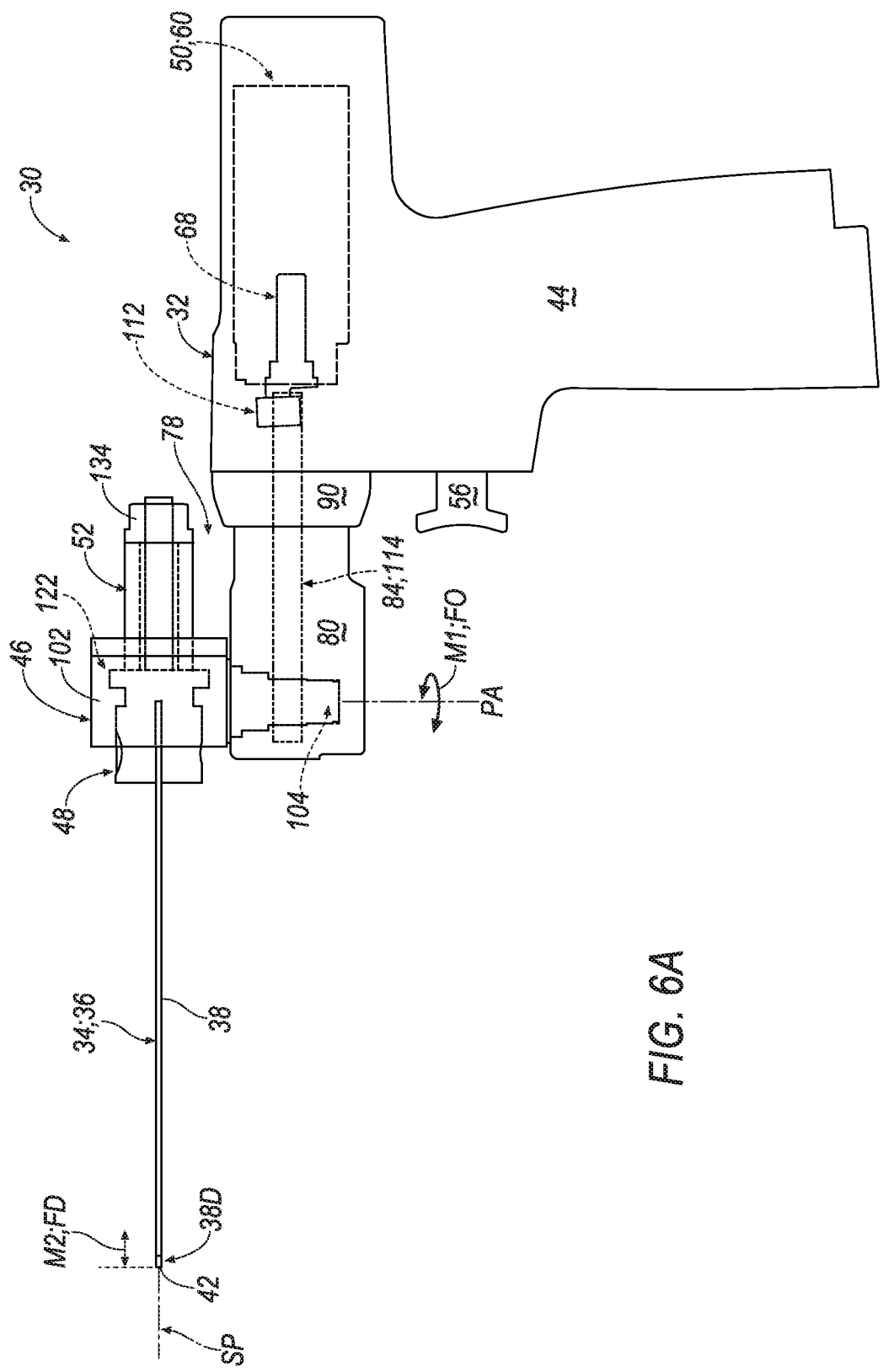

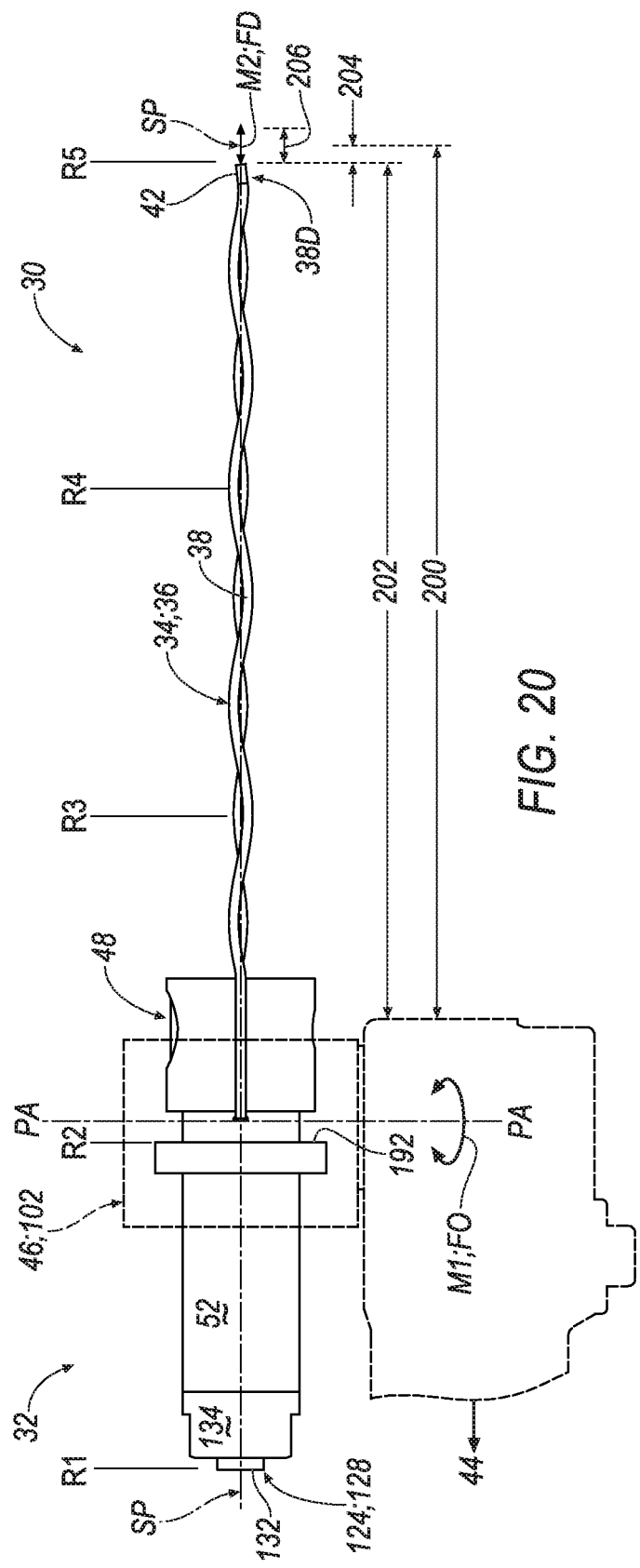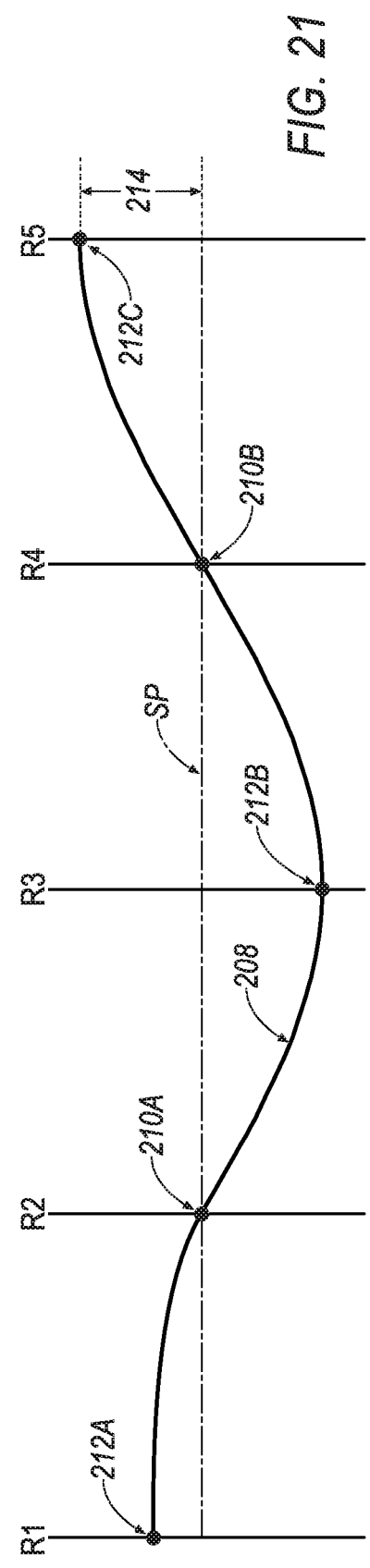

SURGICAL SYSTEMS AND TOOLS FOR MOVING ENERGY APPLICATORS IN SUPERIMPOSED MODES

CROSS-REFERENCE TO RELATED APPLICATIONS

This patent application claims priority to and all advantages of U.S. Provisional Patent Application No. 62/651,290 filed Apr. 2, 2018, the entire contents of which are incorporated herein by reference.

BACKGROUND

Conventional medical and surgical procedures routinely involve the use of systems and tools which allow surgeons to approach and manipulate surgical sites. To this end, surgical tools are typically configured to move an energy applicator (e.g., a drill bit, a bur, a saw blade, and the like) to promote cutting, removing, or otherwise manipulating tissue. By way of illustration, surgical tools configured as sagittal saws are utilized in orthopedic procedures to cut relatively hard tissue (e.g., bone) by oscillating a saw blade back and forth within a sagittal plane. Here, teeth formed at a distal blade end of the saw blade engage against and cut into tissue as the saw blade oscillates in the sagittal plane.

It will be appreciated that predictable performance of surgical tools and energy applicators is desirable. However, depending on the type of tissue being cut and the specific configuration of the surgical tool and/or the energy applicator, decreased or inconsistent cutting performance may occur during use as certain medical and surgical procedures are carried out. By way of illustrative example, for surgical tools which are configured as sagittal saws, fragments of cut tissue (sometimes referred to as "swarf") may accumulate between the teeth of the saw blade, thereby resulting in a reduced cutting speed, increased friction and heat generation at the surgical site. Furthermore, cutting performance which is generally less predictable makes the surgical tool more difficult for the surgeon to handle and control which, in turn, may result in an increased tendency for the saw blade to "skive and dive" off the sagittal plane.

While surgical tools such as sagittal saws have generally performed well for their intended use, there remains a need in the art for addressing one or more of the deficiencies described above.

BRIEF DESCRIPTION OF THE DRAWINGS

Advantages of the embodiments disclosed herein will be readily appreciated as the same becomes better understood after reading the subsequent description taken in connection with the accompanying drawings.

FIG. 6A is a schematic view depicting the embodiment of the surgical system shown in FIGS. 1-5.

FIG. 20 is a partial, right-side schematic view of the surgical system arranged as depicted in FIG. 18A.

FIG. 21 is a graph depicting a standing wave defined by resonance of the saw blade as depicted in FIGS. 18A and 20, the standing wave shown passing through the sagittal plane at a node and propagating to an antinode arranged adjacent to a distal blade end of the saw blade.

DETAILED DESCRIPTION OF THE EMBODIMENTS

Figure 1:
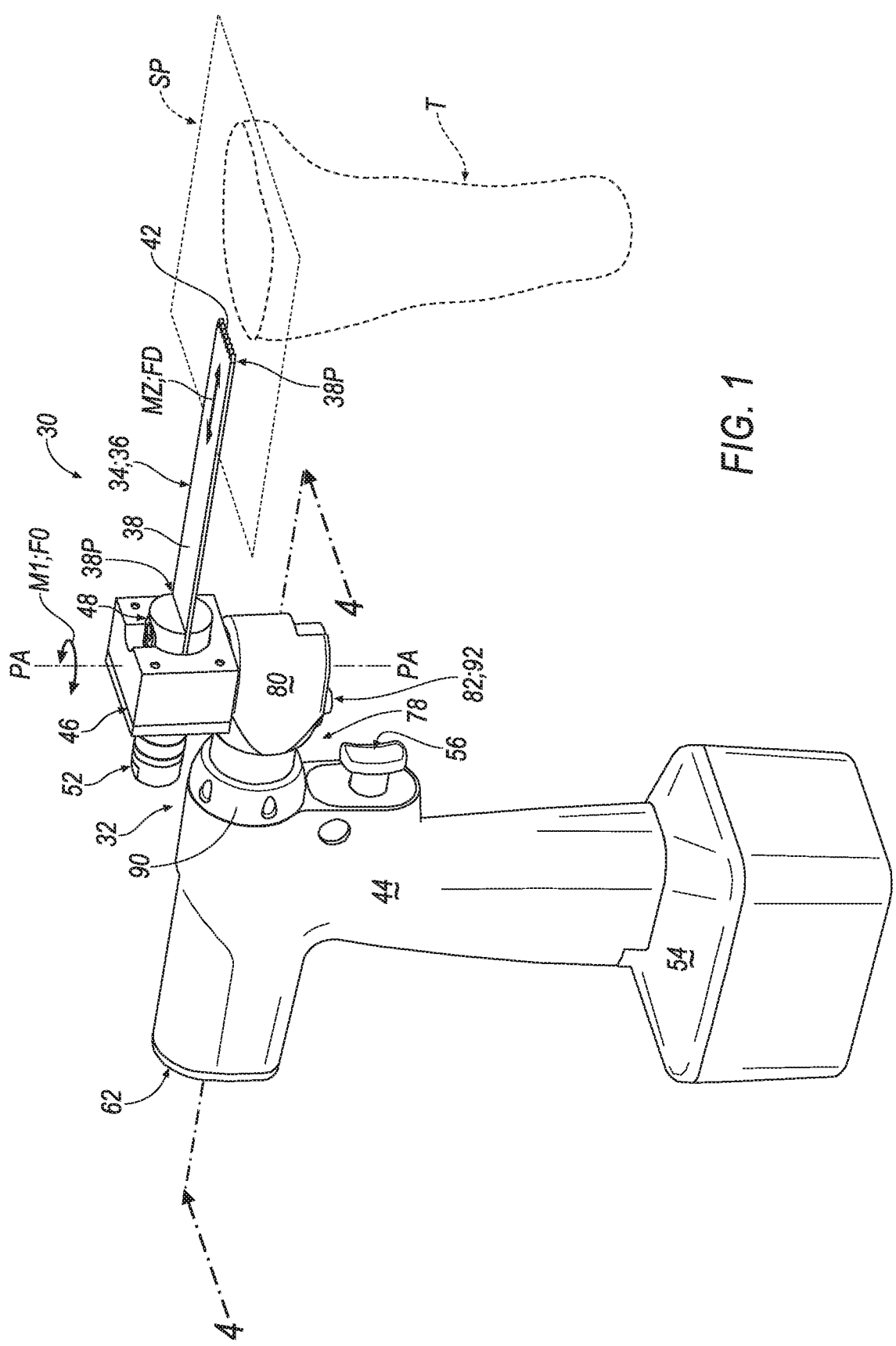
FIG. 1 is a perspective view of a surgical system according to one embodiment, shown comprising a saw blade secured to a surgical tool having a handpiece body and a head subassembly supporting an ultrasonic transducer, a carrier, and a retainer for concurrent oscillating movement about a pivot axis with the retainer releasably securing the saw blade for movement in a sagittal plane relative to the handpiece body.

A surgical tool for use in moving a saw blade in a sagittal plane, the saw blade having a distal blade end with teeth, comprises a handpiece body, a carrier, a retainer, an actuator and an ultrasonic transducer. The carrier is operatively attached to the handpiece body. The carrier is configured for oscillating movement about a pivot axis. The retainer is operatively attached to the carrier for concurrent oscillating movement about the pivot axis. The retainer is configured to releasably secure the saw blade in the sagittal plane relative to the handpiece body. The actuator is coupled to the handpiece body. The actuator is configured to selectively oscillate the carrier relative to the handpiece body such that the retainer and the saw blade pivot back and forth about the pivot axis within the sagittal plane. The ultrasonic transducer is operatively attached to the handpiece body. The ultrasonic transducer is configured to selectively generate ultrasonic energy to resonate the saw blade such that the teeth at the distal blade end reciprocate proximally and distally within the sagittal plane.

The ultrasonic transducer may be coupled to the carrier for concurrent oscillating movement.

The ultrasonic transducer may comprise a piezoelectric transducer.

The surgical tool may further comprise a waveguide body interposed in force-translating relation between the retainer and the ultrasonic transducer to direct ultrasonic energy generated by the ultrasonic transducer toward the retainer.

The waveguide body may comprise a mount portion and a flange portion. The mount portion may secure the ultrasonic transducer to the waveguide body. The flange portion may be arranged between the retainer and the mount portion, with the flange portion operatively attached to the carrier such that the waveguide body and the carrier oscillate concurrently.

The carrier may comprise a pivot housing and a pivot shaft. The pivot housing may be operatively attached to the flange portion of the waveguide body. The pivot shaft may be coupled to the pivot housing for concurrent oscillating movement with the pivot housing.

The pivot shaft may define the pivot axis.

The flange portion of the waveguide body may be arranged closer to the pivot axis than the mount portion of the waveguide.

The surgical tool may further comprise a head body operatively attached to the handpiece body to support the carrier for oscillating movement about the pivot axis relative to the handpiece body.

The actuator may comprise a motor configured to selectively generate rotational torque about a motor axis. The motor axis may be substantially perpendicular to the pivot axis.

The surgical tool may further comprise a linkage interposed between the motor and the carrier to translate rotation about the motor axis into oscillating movement about the pivot axis.

The carrier may further comprise a pivot shaft. The motor may comprise an output shaft with an eccentric head arranged for orbital motion about the motor axis. The linkage may comprise a connecting rod interposed between the pivot shaft and the eccentric head to translate rotation of the output shaft about the motor axis into oscillating movement of the pivot shaft about the pivot axis.

The surgical tool may further comprise a controller disposed in communication with the actuator and the ultrasonic transducer. The controller may be configured to drive the actuator such that the carrier oscillates at an oscillating frequency. The controller may be further configured to drive the ultrasonic transducer such that ultrasonic energy may be generated at a drive frequency which is greater than the oscillating frequency.

The controller may be further configured to drive the ultrasonic transducer and the actuator simultaneously.

The drive frequency may be at least 50 times greater than the oscillating frequency.

The drive frequency may be at least 150 times greater than the oscillating frequency.

The drive frequency may be between 18 kHz and 40 kHz

The oscillating frequency may be between 16 Hz and 330 Hz.

The surgical tool may further comprise an input control operatively attached to the handpiece body, arranged for engagement by a user, and disposed in communication with the controller. The controller may be configured to communicate an actuator drive signal to the actuator in response to engagement of the input control by the user to facilitate driving the actuator, and to communicate a transducer drive signal to the ultrasonic transducer in response to engagement of the input control by the user to facilitate generating ultrasonic energy with the ultrasonic transducer.

The controller may be further configured to adjust the actuator drive signal proportionally with respect to engagement of the input control by the user.

The controller may be further configured to adjust the transducer drive signal to substantially maintain resonance at the drive frequency.

A surgical system for use in cutting tissue in a sagittal plane comprises a saw blade and a surgical tool to move the saw blade. The saw blade may engage tissue in the sagittal plane. The saw blade comprises a blade body extending between a proximal blade end and a distal blade end. A retention mount is formed in the blade body adjacent to the proximal blade end. At least one tooth is formed at the distal blade end to engage tissue within the sagittal plane. The surgical tool comprises a handpiece body, a carrier, a retainer, an actuator, and an ultrasonic transducer. The carrier is operatively attached to the handpiece body. The carrier is configured for oscillating movement about a pivot axis. A retainer is operatively attached to the carrier for concurrent oscillating movement about the pivot axis. The retainer is configured to releasably engage the retention mount of the saw blade to secure the saw blade in the sagittal plane relative to the handpiece body. The actuator is coupled to the handpiece body. The actuator is configured to selectively oscillate the carrier relative to the handpiece body such that the retainer and the saw blade pivot back and forth about the pivot axis within the sagittal plane. The ultrasonic transducer is operatively attached to the handpiece body. The ultrasonic transducer is configured to selectively generate ultrasonic energy to resonate the saw blade such that the teeth at the distal blade end reciprocate proximally and distally within the sagittal plane.

The surgical tool may further comprise a waveguide body interposed in force-translating relation between the retainer and the ultrasonic transducer to direct ultrasonic energy generated by the ultrasonic transducer toward the retainer.

The waveguide body may comprise a mount portion and a flange portion. The mount portion may secure the ultrasonic transducer to the waveguide body. The flange portion may be arranged between the retainer and the mount portion, with the flange portion operatively attached to the carrier such that the waveguide body and the carrier oscillate concurrently.

The waveguide body and the saw blade may resonate to define a standing wave in response to ultrasonic energy generated by the ultrasonic transducer. The standing wave may propagate toward the distal blade end of the saw blade such that the teeth at the distal blade end reciprocate proximally and distally within the sagittal plane.

An amplitude of the standing wave taken adjacent to the distal blade end of the saw blade may correspond to half of a reciprocation distance defined as the teeth at the distal blade end reciprocate proximally and distally within the sagittal plane.

The standing wave may pass through the sagittal plane to define a node arranged adjacent to the flange portion of the waveguide body so as to at least partially inhibit ultrasonic energy from being transferred from the ultrasonic transducer into the handpiece body.

The standing wave may pass through the sagittal plane to define one or more nodes arranged between the ultrasonic transducer and the teeth of the saw blade.

The standing wave may define at least one antinode arranged adjacent to the distal blade end of the saw blade to facilitate reciprocation of the teeth of the saw blade within the sagittal plane in response to ultrasonic energy generated by the ultrasonic transducer.

The antinode may be arranged adjacent to the distal blade end of the saw blade and may define an amplitude of the standing wave which corresponds to half of a reciprocation distance defined as the teeth at the distal blade end reciprocate proximally and distally within the sagittal plane.

The waveguide body may comprise a mount portion and a flange portion. The mount portion may secure the ultrasonic transducer to the waveguide body. The flange portion may be arranged between the retainer and the mount portion, with the flange portion operatively attached to the carrier such that the waveguide body and the carrier oscillate concurrently.

The carrier may comprise a pivot housing and a pivot shaft. The pivot housing may be operatively attached to the flange portion of the waveguide body. The pivot shaft may be coupled to the pivot housing for concurrent oscillating movement with the pivot housing.

The pivot shaft may define the pivot axis.

The flange portion of the waveguide body may be arranged closer to the pivot axis than the mount portion of the waveguide.

The ultrasonic transducer may be coupled to the carrier for concurrent oscillating movement.

The ultrasonic transducer may comprise a piezoelectric transducer.

The surgical system may further comprise a waveguide body interposed in force-translating relation between the retainer and the ultrasonic transducer to direct ultrasonic energy generated by the ultrasonic transducer toward the retainer.

The surgical system may further comprise a head body operatively attached to the handpiece body to support the carrier for oscillating movement about the pivot axis relative to the handpiece body.

The actuator may comprise a motor configured to selectively generate rotational torque about a motor axis.

The motor axis may be substantially perpendicular to the pivot axis.

The surgical system may further comprise a linkage interposed between the motor and the carrier to translate rotation about the motor axis into oscillating movement about the pivot axis.

The carrier may further comprise a pivot shaft. The motor may comprise an output shaft with an eccentric head arranged for orbital motion about the motor axis, and the linkage may comprise a connecting rod interposed between the pivot shaft and the eccentric head to translate rotation of the output shaft about the motor axis into oscillating movement of the pivot shaft about the pivot axis.

The surgical system may further comprise a controller disposed in communication with the actuator and the ultrasonic transducer. The controller may be configured to drive the actuator such that the carrier oscillates at an oscillating frequency. The controller may be further configured to drive the ultrasonic transducer such that ultrasonic energy is generated at a drive frequency which is greater than the oscillating frequency.

The controller may be further configured to drive the ultrasonic transducer and the actuator simultaneously.

The drive frequency may be at least 50 times greater than the oscillating frequency.

The drive frequency may be at least 150 times greater than the oscillating frequency.

The drive frequency may be between 18 kHz and 40 kHz

The oscillating frequency may be between 16 Hz and 330 Hz.

The surgical system may further comprise an input control operatively attached to the handpiece body, arranged for engagement by a user, and disposed in communication with the controller. The controller may be configured to communicate an actuator drive signal to the actuator in response to engagement of the input control by the user to facilitate driving the actuator, and to communicate a transducer drive signal to the ultrasonic transducer in response to engagement of the input control by the user to facilitate generating ultrasonic energy with the ultrasonic transducer.

The controller may be further configured to adjust the actuator drive signal proportionally with respect to engagement of the input control by the user.

The controller may be further configured to adjust the transducer drive signal to substantially maintain resonance at the drive frequency.

A surgical tool for use in moving an energy application in a sagittal plane comprises a handpiece body, a carrier, a retainer, an actuator and a transducer. The carrier is operatively attached to the handpiece body. The carrier is configured for oscillating movement about a pivot axis. The retainer is operatively attached to the carrier for concurrent oscillating movement about the pivot axis relative to the handpiece body. The actuator is coupled to the handpiece body. The actuator is configured to selectively oscillate the carrier relative to the handpiece body such that the retainer pivots back and forth about the pivot axis. A transducer is operatively attached to the handpiece body. The transducer is configured to selectively generate ultrasonic energy to resonate the retainer such that the retainer reciprocates proximally and distally within the sagittal plane.

A surgical tool for use in moving a saw blade in a sagittal plane, the saw blade having a distal blade end with teeth, comprises a handpiece body, a carrier, a retainer, an actuator and a transducer. The carrier is operatively attached to the handpiece body. The carrier is configured for oscillating movement about a pivot axis. The retainer is operatively attached to the carrier for concurrent oscillating movement about the pivot axis. The retainer is configured to releasably secure the saw blade in the sagittal plane relative to the handpiece body. The actuator is coupled to the handpiece body. The actuator is configured to selectively oscillate the carrier relative to the handpiece body such that the retainer and the saw blade pivot back and forth about the pivot axis within the sagittal plane at an oscillating frequency. The transducer is operatively attached to the handpiece body. The transducer is configured to selectively move the saw blade such that the teeth at the distal blade end reciprocate proximally and distally within the sagittal plane at a drive frequency which is greater than the oscillating frequency.

A surgical tool for use in cutting tissue in a sagittal plane comprises a head body, a carrier, a waveguide body and an ultrasonic transducer. The carrier includes a pivot body and a pivot shaft. The pivot shaft is fixed to the pivot body for unitary movement therewith and is pivotably connected to the head body. The waveguide body includes a retainer portion, a mount portion and a flange portion. The retainer portion comprises a first brace element including a first brace surface and a second brace element having a second brace surface facing the first brace surface. The brace surfaces define a slot therebetween for receipt of a blade. The flange portion is disposed between and connects the retainer and the mount portion and is fixed to the pivot body. The ultrasonic transducer is secured to the mount portion.

The retainer portion, the mount portion and the flange portion of the waveguide body may be formed together as a unitary one-piece unit.

The mount portion may have a substantially cylindrical profile. The ultrasonic transducer may comprise a plurality of piezoelectric transducers disposed over the mount portion and compressed against the flange.

With reference to the drawings, where like numerals are used to designate like structure throughout the several views, a surgical system is shown at 30 in FIG. 1. The surgical system 30 is configured to engage tissue T of a patient in connection with various types of medical and/or surgical procedures (e.g., total knee arthroplasty). To this end, the surgical system 30 comprises a surgical tool 32 which drives or otherwise effects movement of an energy applicator 34 in superimposed modes to promote cutting, removing, or otherwise manipulating tissue T, as described in greater detail below.

The representative embodiment of the energy applicator 34 illustrated throughout the drawings is realized as a saw blade 36 supported for movement in a sagittal plane SP by the surgical tool 32 (sometimes referred to as a "sagittal saw"). The surgical tool 32 moves the saw blade 36 in two modes: a first mode M1 where the saw blade 36 oscillates back and forth within the sagittal plane SP about a pivot axis PA, and a second mode M2 where the saw blade 36 reciprocates proximally and distally within the sagittal plane SP. The first and second modes M1, M2 are superimposed such that the saw blade 36 can reciprocate and oscillate concurrently within the sagittal plane SP. More specifically, in the illustrated embodiment, movement in the second mode M2 occurs at a higher frequency than movement in the first mode M1 such that a plurality of reciprocations occur during a single oscillation which, as is described in greater detail below, affords significant advantages in connection with, among other things, enhanced cutting consistency and reliability, reduced wear to the saw blade 36, and improved overall performance of the surgical tool 32. Those having ordinary skill in the art will appreciate that the term "sagittal saw" is a non-limiting term of art and, thus, the terms "sagittal plane" and/or "sagittal" do not necessarily correspond to any particular portion of the patient's anatomy as used herein. Moreover, in contrast to an "osteotomy plane," which has a measurable thickness defined such as by one or more geometric properties of the saw blade 36, the term "sagittal plane" used herein refers to a flat, two-dimensional surface which has no thickness and may have an infinite length and/or width. Thus, movement of the saw blade 36 in the sagittal plane SP may be defined in any suitable way where at least a portion of the saw blade 36 contacts or intersects the sagittal plane SP.

While the illustrated surgical system 30 is configured to move the saw blade 36 within the sagittal plane SP in the first and second modes M1, M2, other types of surgical tools 32 and/or energy applicators 34 which move in superimposed modes are contemplated by the present disclosure. By way of non-limiting example, the energy applicator 34 could be realized as a drill bit, a bur, a saw, a shaver, and the like which is moved by the surgical tool 32 in superimposed modes defined rotation, oscillation, translation, reciprocation, percussion, vibration, and/or combinations thereof. Furthermore, while the embodiments disclosed herein are directed toward movement in the first and second modes M1, M2, it will be appreciated that the surgical tool 32 could be configured to move the energy applicator 34 in additional modes (not shown) without departing from the scope of the present disclosure. Other configurations are contemplated.

Figure 2:
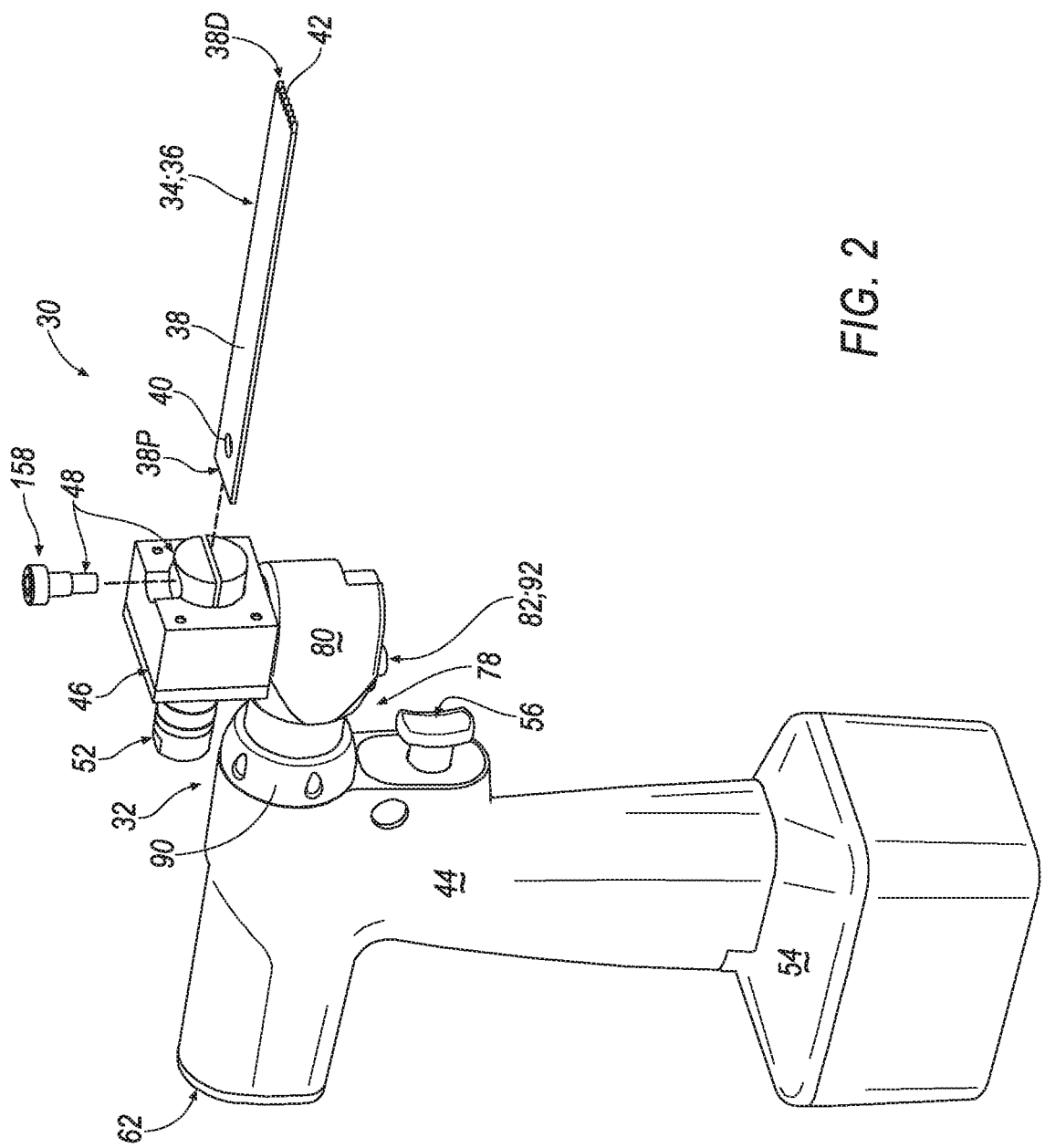
FIG. 2 is a partially-exploded perspective view of the surgical system of FIG. 1, shown with the saw blade spaced from the retainer of the surgical tool.
Figure 3A:
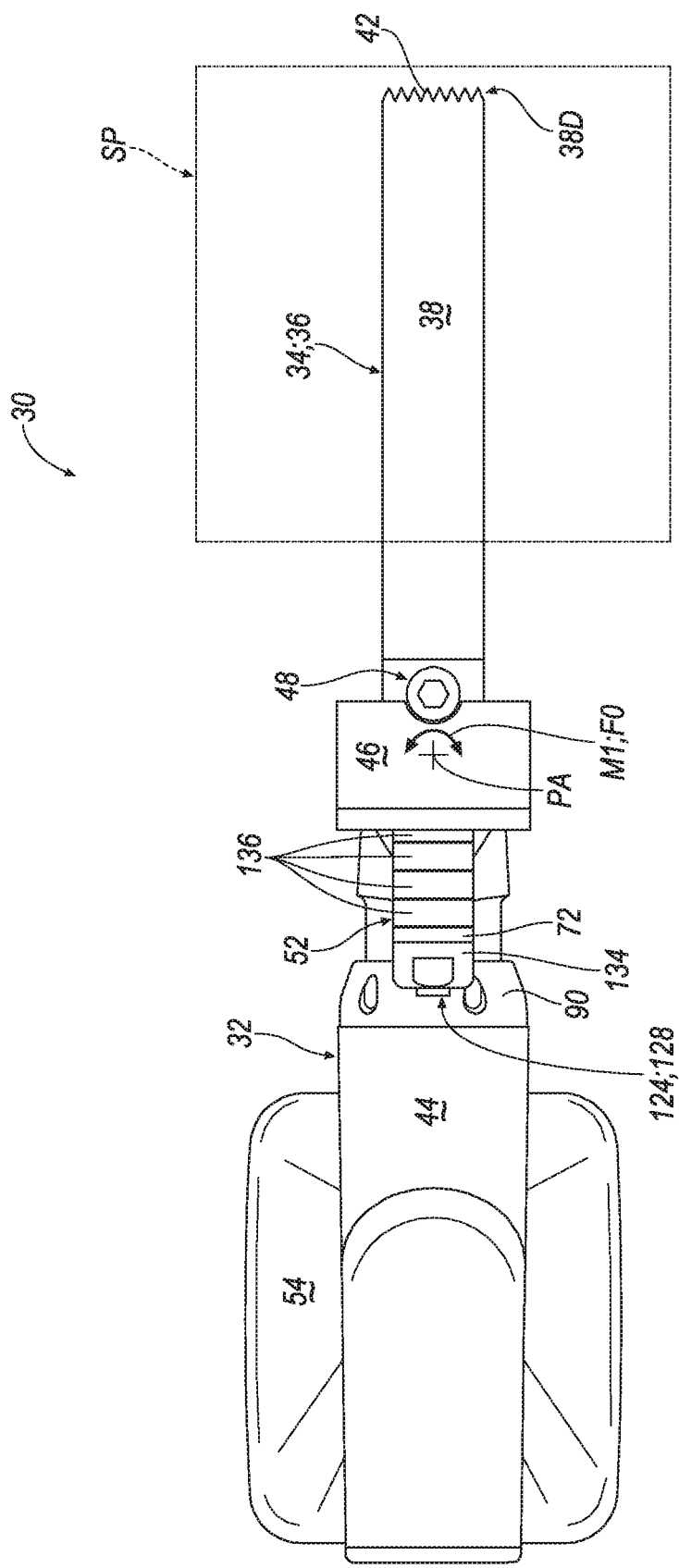
FIG. 3A is a top-side plan view of the surgical system of FIGS. 1-2.
Figure 3B:
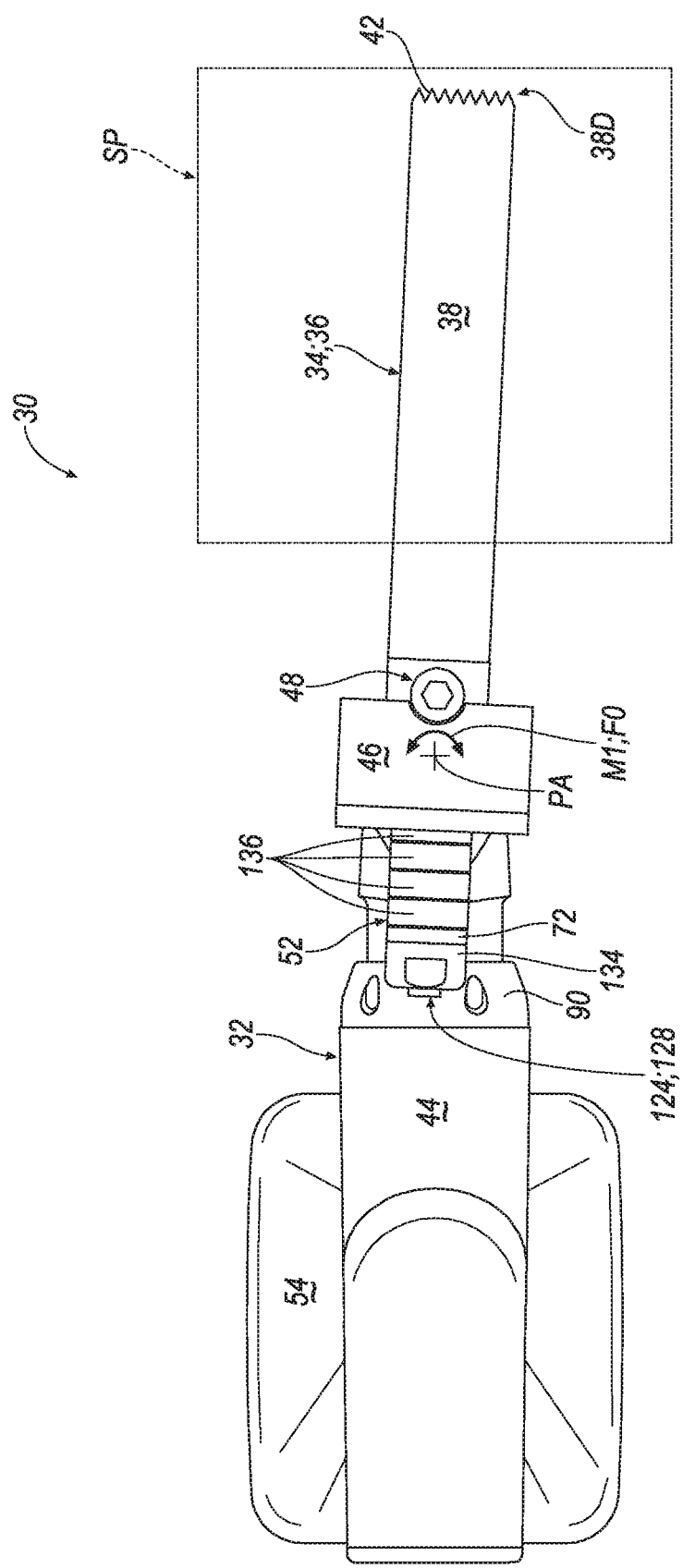
FIG. 3B is another top-side plan view of the surgical system of FIG. 3A, shown with the saw blade pivoted in a first direction about the pivot axis.
Figure 3C:
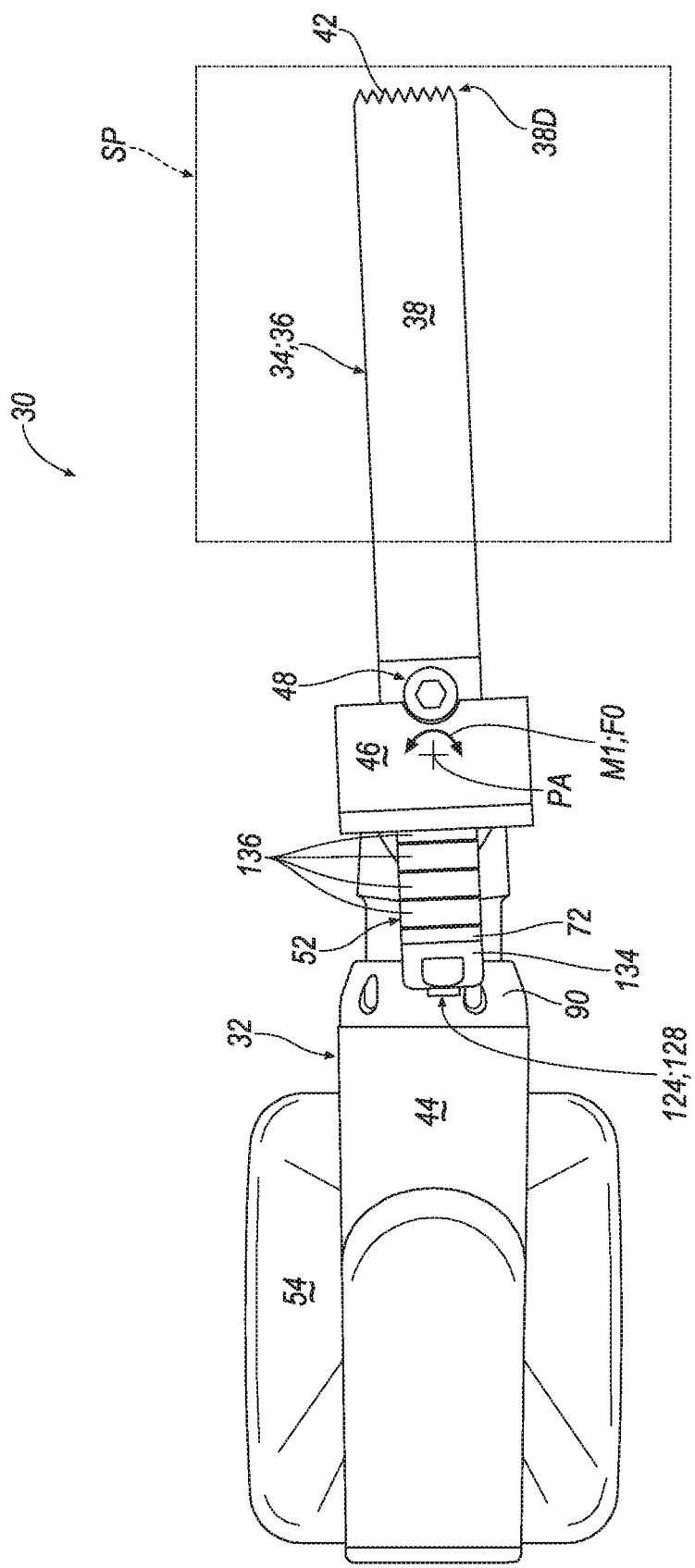
FIG. 3C is another top-side plan view of the surgical system of FIGS. 3A-3B, shown with the saw blade pivoted in a second direction about the pivot axis.

Referring now to FIGS. 1-5, as noted above, the illustrated surgical system 30 generally comprises the surgical tool 32 and a releasably-attachable saw blade 36 to cut various types of tissue T (e.g., bone) in the sagittal plane SP. As is best depicted in FIG. 2, the saw blade 36 has a generally, i.e., substantially, planar and rectangular blade body 38 which extends between a proximal blade end 38P and a distal blade end 38D. A retention mount, generally indicated at 40, is formed in the blade body 38 adjacent to the proximal blade end 38P to facilitate releasable attachment to the surgical tool 32. One or more teeth 42 are formed at the distal blade end 38D to engage against and cut tissue T (see FIG. 1) within the sagittal plane SP as the surgical tool 32 moves the saw blade 36 in the first and second modes M1, M2. The blade body 38, the retention mount 40, and the teeth 42 of the saw blade 36 will each be described in greater detail below.

With continued reference to FIGS. 1-5, the surgical tool 32 generally comprises a handpiece body 44, a carrier 46, a retainer 48, an actuator 50 (see FIG. 4), and a transducer 52 which cooperate to facilitate movement of the saw blade 36 within the sagittal plane SP in the first and second modes M1, M2. The carrier 46 is operatively attached to the handpiece body 44 and is configured for oscillating movement about the pivot axis PA (see FIGS. 3A-3C). The retainer 48 is operatively attached to the carrier 46 for concurrent oscillating movement about the pivot axis PA, and is configured to releasably engage the retention mount 40 of the saw blade 36 to secure the saw blade 36 in the sagittal plane SP relative to the handpiece body 44. The actuator 50 is coupled to the handpiece body 44 and is configured to selectively oscillate the carrier 46 relative to the handpiece body 44 such that the retainer 48 and the saw blade 36 pivot back and forth about the pivot axis PA within the sagittal plane SP. In the illustrated embodiment, the transducer 52 is operatively attached to the handpiece body 44 and is configured to selectively generate ultrasonic energy to resonate the saw blade 36 such that the teeth 42 at the distal blade end 38D reciprocate proximally and distally within the sagittal plane SP, as described in greater detail below in connection with FIGS. 17A-21. The handpiece body 44, the carrier 46, the retainer 48, the actuator 50, and the ultrasonic transducer 52 of the surgical tool 32 will each be described in greater detail below.

Referring now to FIGS. 1-18C, the illustrated embodiments of the surgical system 30 are configured for use in various types of medical and/or surgical procedures which involve making substantially planar cuts through relatively hard tissue T along the sagittal plane SP, as noted above. To this end, the surgical tool 32 is realized as a portable, hand-held instrument which employs a rechargeable battery 54, an input control 56, and a controller 58 (see FIG. 4) to facilitate powering and selectively driving the actuator 50 and the ultrasonic transducer 52 during use to effect movement in the first and second modes M1, M2, as described in greater detail below. In the illustrated embodiment, the actuator 50 comprises an electric motor 60 supported within the handpiece body 44 to selectively generate rotational torque about a motor axis MA. Here, the rotational torque generated by the motor 60 is used to facilitate oscillating movement of the carrier 46 about the pivot axis PA to move the saw blade 36 back and forth within the sagittal plane SP in the first mode M1. However, as will be appreciated from the subsequent description below, other types and arrangements of actuators 50 are contemplated by the present disclosure.

Figure 4:
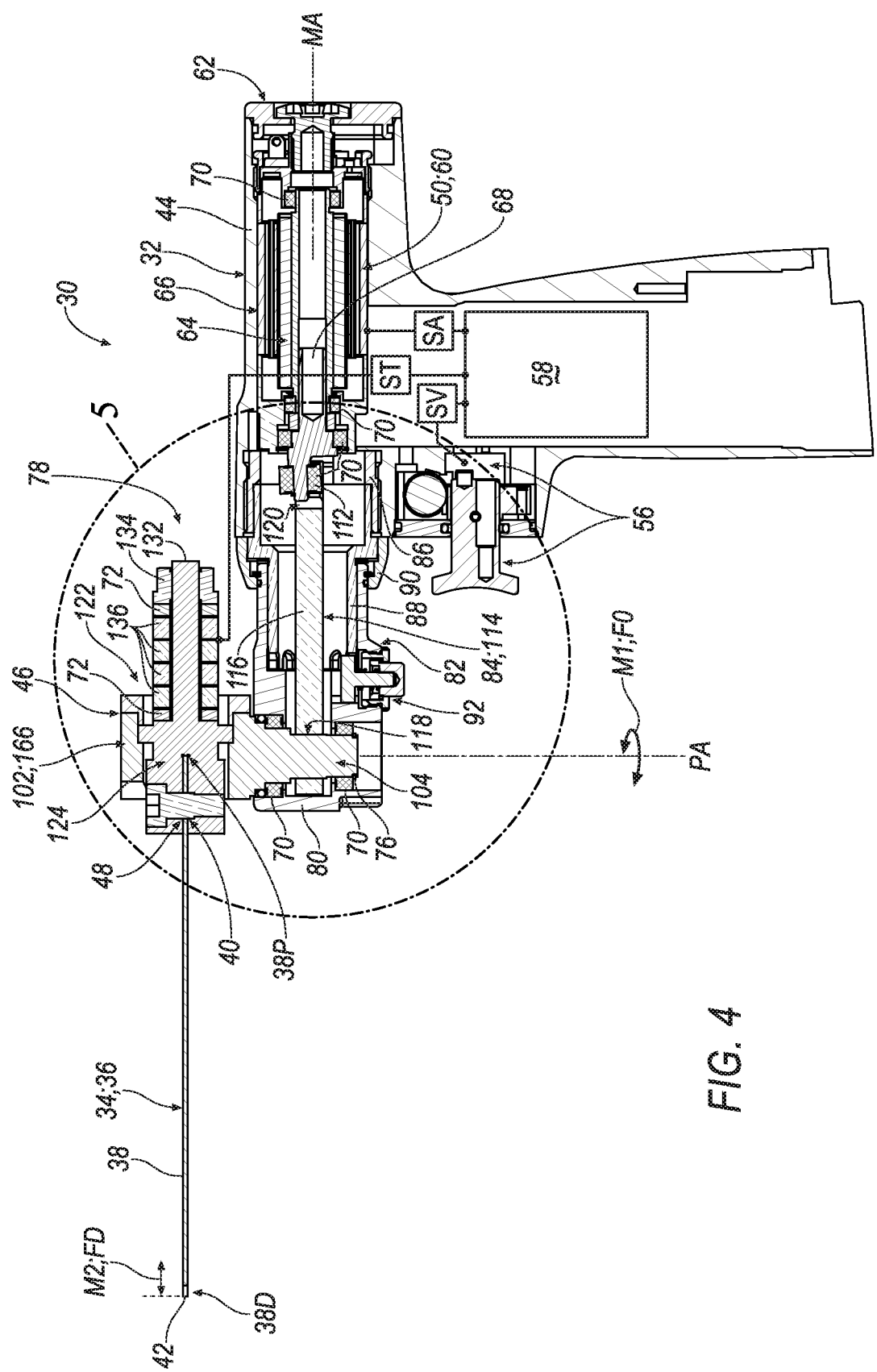
FIG. 4 is a sectional view taken along line 4-4 in FIG. 1, shown with portions of the surgical tool omitted for clarity.

As is depicted schematically in FIG. 4, the controller 58 is disposed in communication with the actuator 50, the ultrasonic transducer 52, the battery 54, and the input control 56 in the illustrated embodiment, such as via wired or wireless electrical communication (not shown in detail). The input control 56 may have a trigger-style configuration projecting from the generally pistol-grip shaped handpiece body 44, is responsive to engagement from a user (e.g., a surgeon), and communicates or otherwise generates commands, signals, and the like to the controller 58 which, in turn, is employed to facilitate driving the actuator 50 and the ultrasonic transducer 52 to effect movement in the respective first and second modes M1, M2. The motor 60, which serves as the actuator 50 in the illustrated embodiment, is configured to selectively generate rotational torque about the motor axis MA in response to commands, signals, and the like received from the controller 58 to effect oscillating movement of the carrier 46, the retainer 48, and the saw blade 36 about the pivot axis PA in the first mode M1, as described in greater detail below. Similarly, the ultrasonic transducer 52 is configured to selectively generate ultrasonic energy in response to commands, signals, and the like received from the controller 58 to effect reciprocating movement of the distal blade end 38D of the saw blade 36 in the second mode M2, as described in greater detail below.

When the user (e.g., a surgeon) actuates the input control 56 to operate the surgical tool 32, the controller 58 directs power from the battery 54 (or some other power source) to the actuator 50 and to the ultrasonic transducer 52 so as to effect movement of the saw blade 36 in the superimposed first and second modes M1, M2. As will be appreciated from the subsequent description below, the handpiece body 44, the actuator 50, the ultrasonic transducer 52, the battery 54, the input control 56, and the controller 58 could each be configured in a number of different ways to facilitate driving the actuator 50 and/or the ultrasonic transducer 52 so as to effect movement in the superimposed first and second modes M1, M2 without departing from the scope of the present disclosure.

The controller 58 is configured to drive the actuator 50 such that the carrier 46 oscillates at an oscillating frequency FO, and is also configured to drive the ultrasonic transducer 52 such that ultrasonic energy is generated at a drive frequency FD which is greater (or "higher") than the oscillating frequency FO. As will be appreciated from the subsequent description of the surgical tool 32 and saw blade 36 below, the drive frequency FD of the second mode M2, defined herein by the reciprocating movement of the distal blade end 38D in the sagittal plane SP, corresponds at least partially to the natural frequency of the saw blade 36 and/or portions of the retainer 48. Moreover, the oscillating frequency FO of the first mode M1, defined herein by the oscillating movement of the carrier 46, the retainer 48, and the saw blade 36 about the pivot axis PA corresponds at least partially to the rotational speed of the motor 60 about the motor axis MA.

In some embodiments, the motor 60 is configured to operate at speeds ranging between approximately 1 k RPM and 20 k RPM. These speeds correspond to oscillating frequencies FO in the first mode M1 ranging between approximately 16.7 Hz and 333.3 Hz. In some embodiments, resonance of the saw blade 36 occurs at relatively high frequencies, ranging from near-ultrasonic (e.g., 18-20 kHz) to ultrasonic (e.g., 20-40 kHz and above). These resonating frequencies correspond to drive frequencies FD in the second mode M2 ranging between approximately 18 kHz and 40 kHz. Thus, it will be appreciated that the drive frequency FD may be an order of magnitude higher than the oscillating frequency FO in some embodiments and under some operating conditions. By way of illustration, where the motor 60 is driven by the controller 58 at a rotational speed of 5 k RPM and advantageous resonance of the saw blade 36 occurs at approximately 20 kHz, the drive frequency FD would be approximately 240 times greater than the oscillating frequency FO. Put differently, during the time it takes for the saw blade 36 to make a single oscillation back and forth about the pivot axis PA within the sagittal plane SP in this illustrative example, the teeth 42 at the distal blade end 38D of the saw blade 36 would reciprocate proximally and distally within the sagittal plane SP approximately 240 times. In some embodiments, the drive frequency FD is at least 50 times greater than the oscillating frequency FO. In some embodiments, the drive frequency FD is at least 150 times greater than the oscillating frequency FO. Other configurations are contemplated.

Referring now to FIG. 4, in some embodiments, the input control 56 generates a variable input signal SV which changes based on the amount of engagement that is applied to the input control 56 by the user. The input signal SV is communicated to the controller 58 which, in turn, is configured to drive the actuator 50 and/or the ultrasonic transducer 52 in different ways depending on and/or in response to changes occurring in the input signal SV. As will be appreciated from the subsequent description below, the input control 56 could be of a number of different types and/or configurations, and could employ any suitable arrangement of sensors, switches, and the like to generate the input signal SV. Moreover, while a single input control 56 is depicted in the representative embodiment of the surgical tool 32 illustrated herein, additional input controls 56 may be employed in certain applications. By way of non-limiting example, one input control 56 could be provided with a spring-biased trigger arranged to move a linear potentiometer which generates a variable input signal SV used to facilitate correspondingly-variable operation of the actuator 50, and another input control 56 could be provided with a latching switch arrangement to generate a "Boolean" input signal SV used to facilitate activating or deactivating the ultrasonic transducer 52. Other configurations are contemplated.

In some embodiments, the controller 58 is configured to communicate an actuator drive signal SA to the actuator 50 in response to engagement of the input control 56 by the user in order to facilitate driving the actuator 50 to oscillate the carrier 46, the retainer 48, and the saw blade 36 about the pivot axis PA and thereby effect movement in the first mode M1. Here, the controller 58 may be further configured to adjust the actuator drive signal SA proportionally with respect to engagement of the input control 56 by the user, such as based on changes occurring in the input signal SV as described above. Other configurations are contemplated.

In some embodiments, the controller 58 is configured to communicate a transducer drive signal ST to the ultrasonic transducer 52 in response to engagement of the input control 56 by the user in order to facilitate generating ultrasonic energy to resonate the saw blade 36 and thereby effect movement in the second mode M2. Here, things like friction, heat, and load acting on the saw blade 36 during use (e.g., as tissue T is cut) necessarily affects the natural frequency of the saw blade 36. Here, the properties of the saw blade 36 (e.g., physical dimensions, material, and the like) can be optimized for particular applications to improve resistance to changes in natural frequency during use. In some embodiments, the controller 58 may be configured to adjust the transducer drive signal ST based on the oscillating frequency FO of the first mode M1, such as to vary how far the distal blade end 38D of the saw blade 36 reciprocates back and forth depending on the oscillating frequency FO. Moreover, because more than one input control 56 may be employed by the surgical tool 32 as noted above, it is conceivable that the controller 58 could adjust the transducer drive signal ST based on an input signal communicated by another input control (not shown) and thereby allow the surgeon to selectively adjust how far the distal blade end 38D of the saw blade 36 reciprocates back and forth. Other configurations are contemplated.

In some embodiments, the controller 58 may be further configured to adjust the transducer drive signal ST so as to substantially maintain resonance at the drive frequency FD, such as by periodically monitoring the saw blade 36 during use for changes in or associated with natural frequency which may occur during use, caused such as by load acting on the teeth 42 as tissue T is cut, heat absorbed by the saw blade 36 generated by friction as the teeth 42 engage tissue T, and the like. To this end, the controller 58 may adjust the transducer drive signal ST based on changes in the impedance of one or more mechanical components of the surgical system 30 during use. By way of non-limiting example, the controller 58 could monitor the impedance of the saw blade 36 and adjust the transducer drive signal ST to compensate for changes in the natural frequency of the saw blade 36 resulting from heat generated as tissue T is cut. The Applicant's Assignee has disclosed one type of system which adjusts the operation of surgical tools based on changes in mechanical impedance in International Patent Application No. PCT/US2014/050034, published as WO2015/021216A1 and titled "SYSTEM AND METHOD FOR DRIVING AN ULTRASONIC HANDPIECE AS A FUNCTION OF THE MECHANICAL IMPEDANCE OF THE HANDPIECE," the disclosure of which is hereby incorporated by reference in its entirety.

While a single controller 58 is employed to facilitate driving both the actuator 50 and the ultrasonic transducer 52 in the illustrated embodiment, other configurations are contemplated by the present disclosure. By way of non-limiting example, separate controllers 58 could be employed to respectively drive, control, or otherwise facilitate operation of the actuator 50 and the ultrasonic transducer 52 independently and/or simultaneously in some embodiments. Furthermore, it will be appreciated that the controller 58 could be configured in a number of different ways, and could include or otherwise be defined by various types of hardware (e.g., processors, integrated circuits, memories, amplifiers, signal generators, signal conditioning circuitry, and the like) and/or software (e.g., programs, algorithms, subroutines, discrete code, firmware, and the like). Other configurations are contemplated.

Furthermore, while the representative embodiment of the surgical tool 32 illustrated herein is configured for hand-held use and employs an "on-board" actuator 50, ultrasonic transducer 52, and controller 58 which are powered via a detachable battery 54, it will be appreciated that other configurations and arrangements are contemplated by the present disclosure. By way of non-limiting example, the surgical tool 32 could be tethered to an external console (not shown) configured to control, power, or otherwise facilitate moving the saw blade 36 in the first and second modes M1, M2 by driving the actuator 50 and/or the ultrasonic transducer 52. Moreover, the actuator 50 could be configured in a number of different ways sufficient to facilitate oscillating the carrier 46 about the pivot axis PA, with or without the use of an electrically-powered motor 60 supported in the handpiece body 44. By way of non-limiting example, the actuator 50 could be a pneumatic motor supported in the handpiece body 44, or supported in an external console to translate rotation and/or oscillation to the carrier 46 via a mechanical tether connecting the external console to the handpiece body 44 (not shown). Other configurations are contemplated.

As noted above, the illustrated embodiment of the actuator 50 comprises an electrically-powered motor 60 to selectively generate rotational torque about the motor axis MA to facilitate oscillating movement of the carrier 46, the retainer 48, and the saw blade 36 about the pivot axis PA in the first mode M1. As is best shown in FIGS. 4 and 7, the motor 60 is generally supported within the handpiece body 44 and is sealed from the outside environment via a back cap 62, which also prevents ingress of contaminants toward the motor 60, the controller 58, and various other components supported within the handpiece body 44.

The motor 60 generally comprises a rotor assembly 64, a stator assembly 66, and an output shaft 68. When the motor 60 is driven by the controller 58, the output shaft 68 and the rotor assembly 64 rotate concurrently about the motor axis MA relative to the stator assembly 66, which is secured to and within the handpiece body 44. An arrangement of bearings 70 rotatably support to the output shaft 68 and the rotor assembly 64 to facilitate rotation relative to the stator assembly 66. In some embodiments, one or more washers 72, bushings 74, and/or circlips 76 may be provided to limit axial movement of one or more components of the motor 60. Other components, such as seals, gaskets, and springs may be provided in some embodiments (not shown in detail).

While the motor 60 is realized as a brushless direct current (BLDC) electric motor in the illustrated embodiment, those having ordinary skill in the art will appreciate that the motor 60 could be configured in a number of different ways without departing from the scope of the present disclosure.

Figure 7:
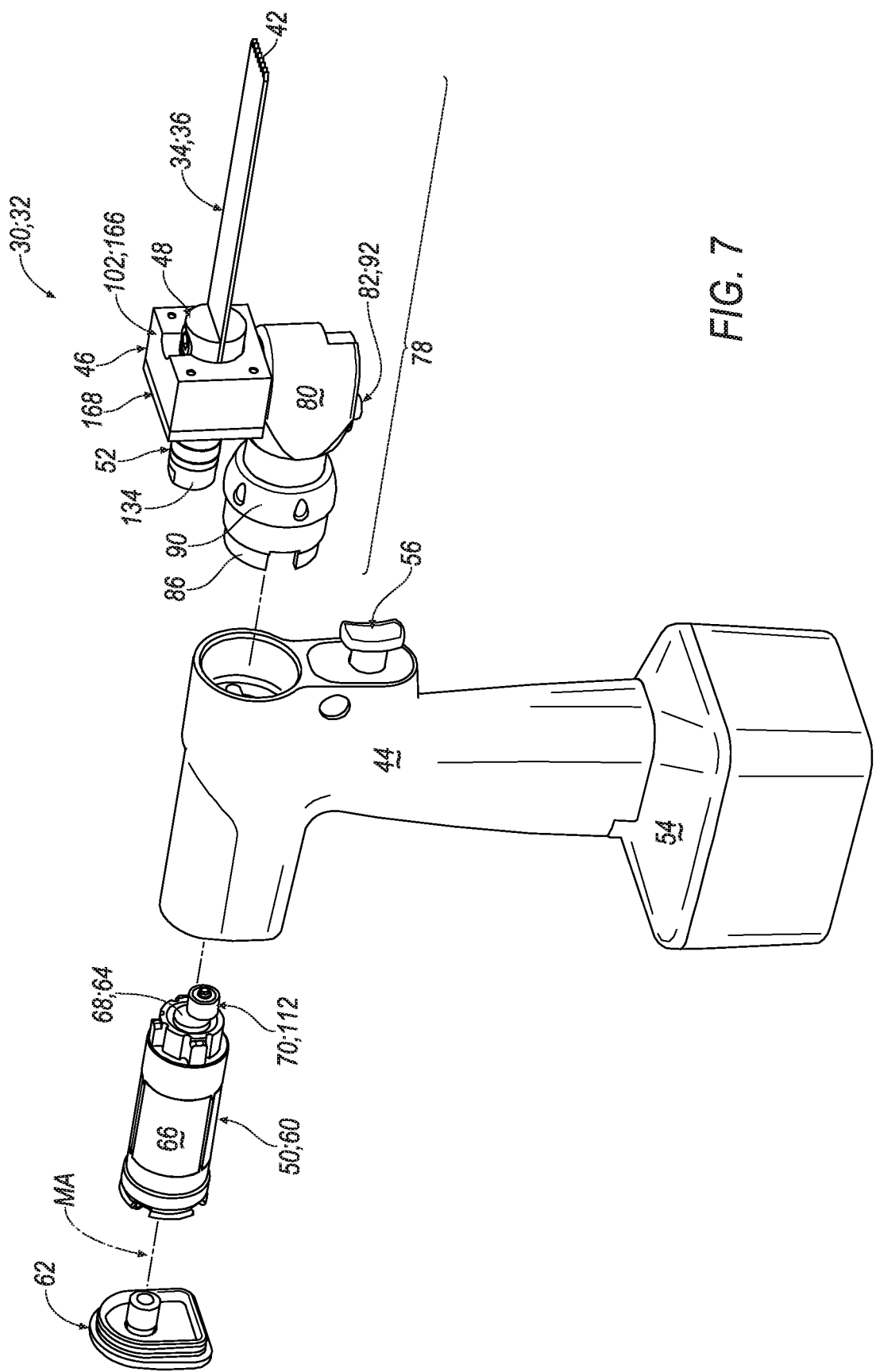
FIG. 7 is a partially-exploded perspective view of the surgical system of FIG. 1, shown with an actuator, a back cap, and the head subassembly spaced from the handpiece body.
Figure 8:
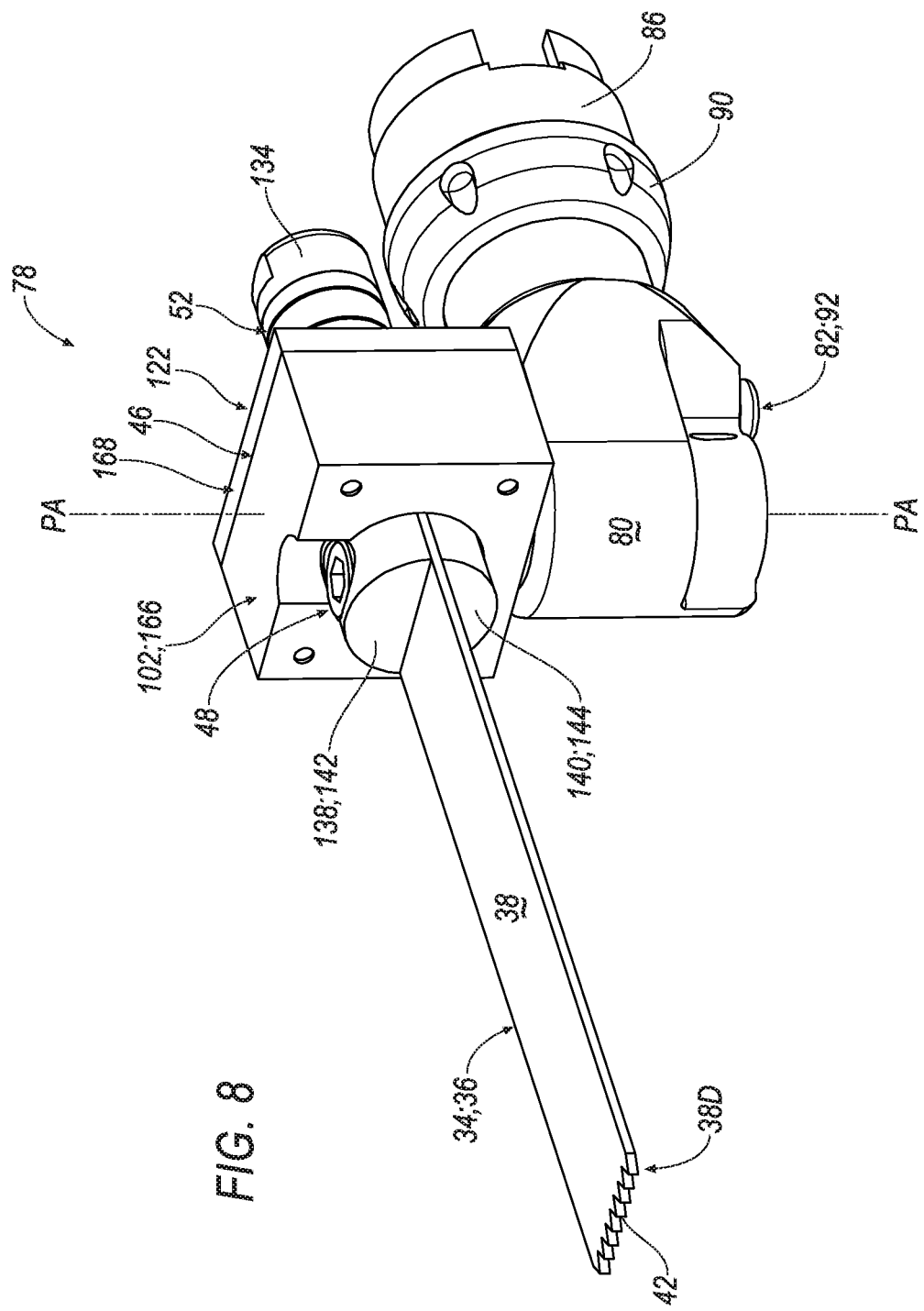
FIG. 8 is a perspective view of the head subassembly of FIG. 7, shown comprising a head body supporting the carrier for oscillating movement about the pivot axis, and an indexing mechanism operatively coupled to the head body.

Referring now to FIGS. 4 and 7-11, the surgical tool 32 comprises a head subassembly 78 which includes and generally affords supports the ultrasonic transducer 52, the carrier 46, and the retainer 48 relative to the handpiece body 44 in the illustrated embodiment (see FIG. 7; compare to FIG. 1). The head subassembly 78 also includes a head body 80, an indexing mechanism 82, and a linkage 84. As is described in greater detail below, the head body 80 and the indexing mechanism generally support the carrier 46 for movement relative to the handpiece body 44, and the linkage 84 is provided to translate rotational torque generated by the motor 60 about the motor axis MA into oscillating movement of the carrier 46, the retainer 48, and the saw blade 36 about the pivot axis PA in the first mode M1.

The head body 80 of the head subassembly 78 rotatably supports the carrier 46 for oscillating movement about the pivot axis PA in the first mode M1, and is operatively attached to the handpiece body 44 via the indexing mechanism 82 in the illustrated embodiment. The indexing mechanism 82, in turn, is interposed between the head body 80 and the handpiece body 44 to facilitate locking the head body 80 relative to the handpiece body 44 in different radial positions about the motor axis MA, thereby allowing the sagittal plane SP to be positioned in correspondingly different positions relative to the handpiece body 44 (different positions not shown). To this end, the indexing mechanism 82 generally comprises a seat 86, a collar 88, a ring member 90, and a detent subassembly 92 in the illustrated embodiment. The seat 86 is coupled to the collar 88 (e.g, via press-fit or threaded engagement) and is configured to releasably attach to the handpiece body 44 (releasable attachment not shown in detail). The collar 88 cooperates with the ring member 90 to secure the head body 80 relative to the handpiece body 44 (see FIG. 4).

Figure 9:
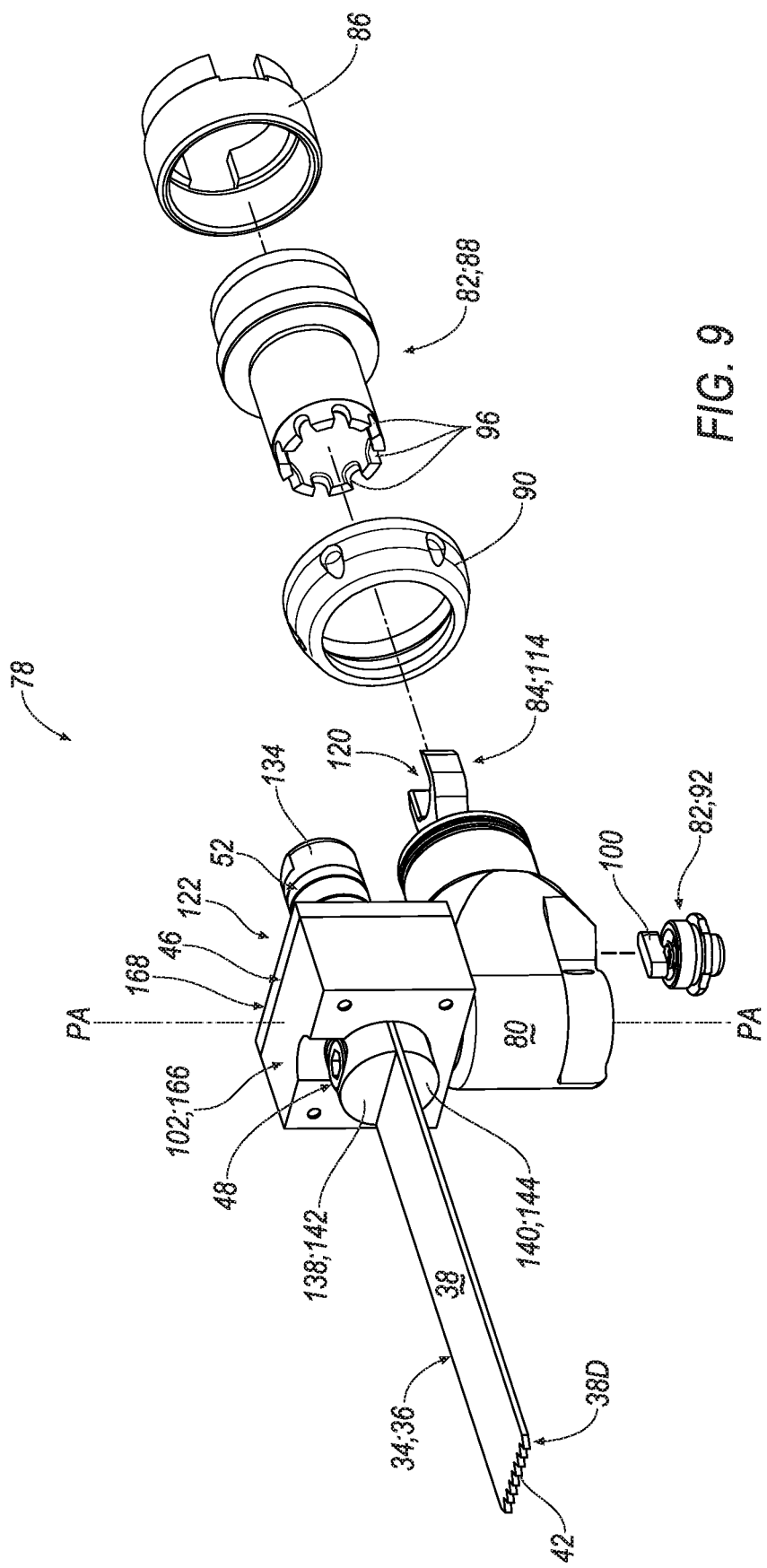
FIG. 9 is a partially-exploded view of the head subassembly of FIG. 8, shown with components of the indexing mechanism spaced from the head body.
Figure 10:
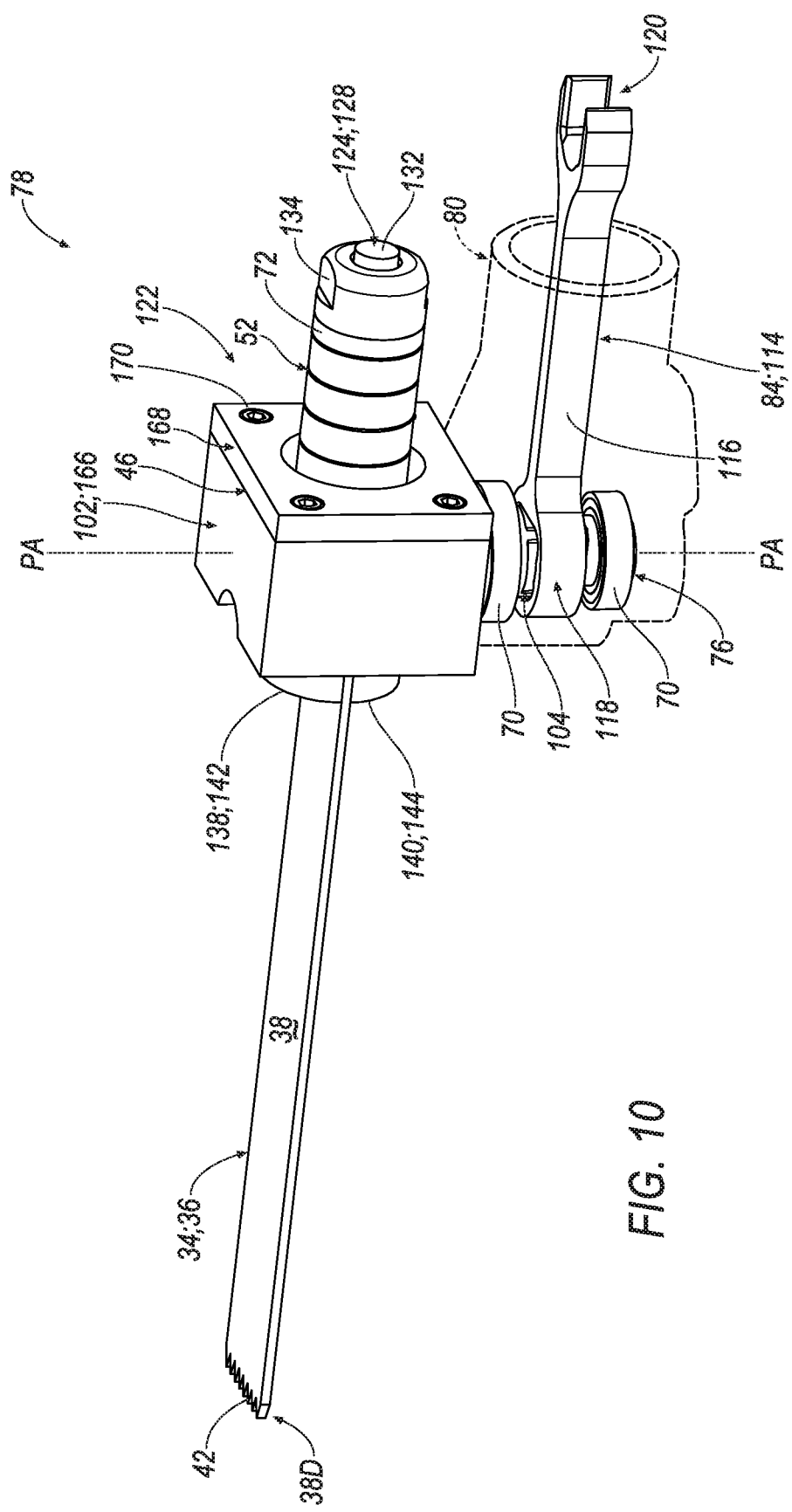
FIG. 10 is a partial perspective view of the head subassembly of FIGS. 7-9, shown with the head body depicted in phantom.

In some embodiments, one or more biasing elements 94 and/or seals 96 may be provided to facilitate operation of the indexing mechanism 82 and help prevent ingress of contaminants toward the various component supported within the handpiece body 44. It will be appreciated that the seat 86 and/or the collar 88 may be fixed to or otherwise formed as a part of the handpiece body 44 in some embodiments. As is best shown in FIGS. 4 and 9, the collar 88 comprises a plurality of notches 98 arranged radially about the motor axis MA, and the detent subassembly 92 comprises a spring-biased plunger, generally indicated at 100, which is shaped to be selectively disposed in any one of the notches 98 so as to lock the head body 80 in different positions relative to the handpiece body 44, as noted above. In some embodiments, the surgical tool 32 could be configured without an indexing mechanism 82. Other configurations are contemplated.

Figure 11:
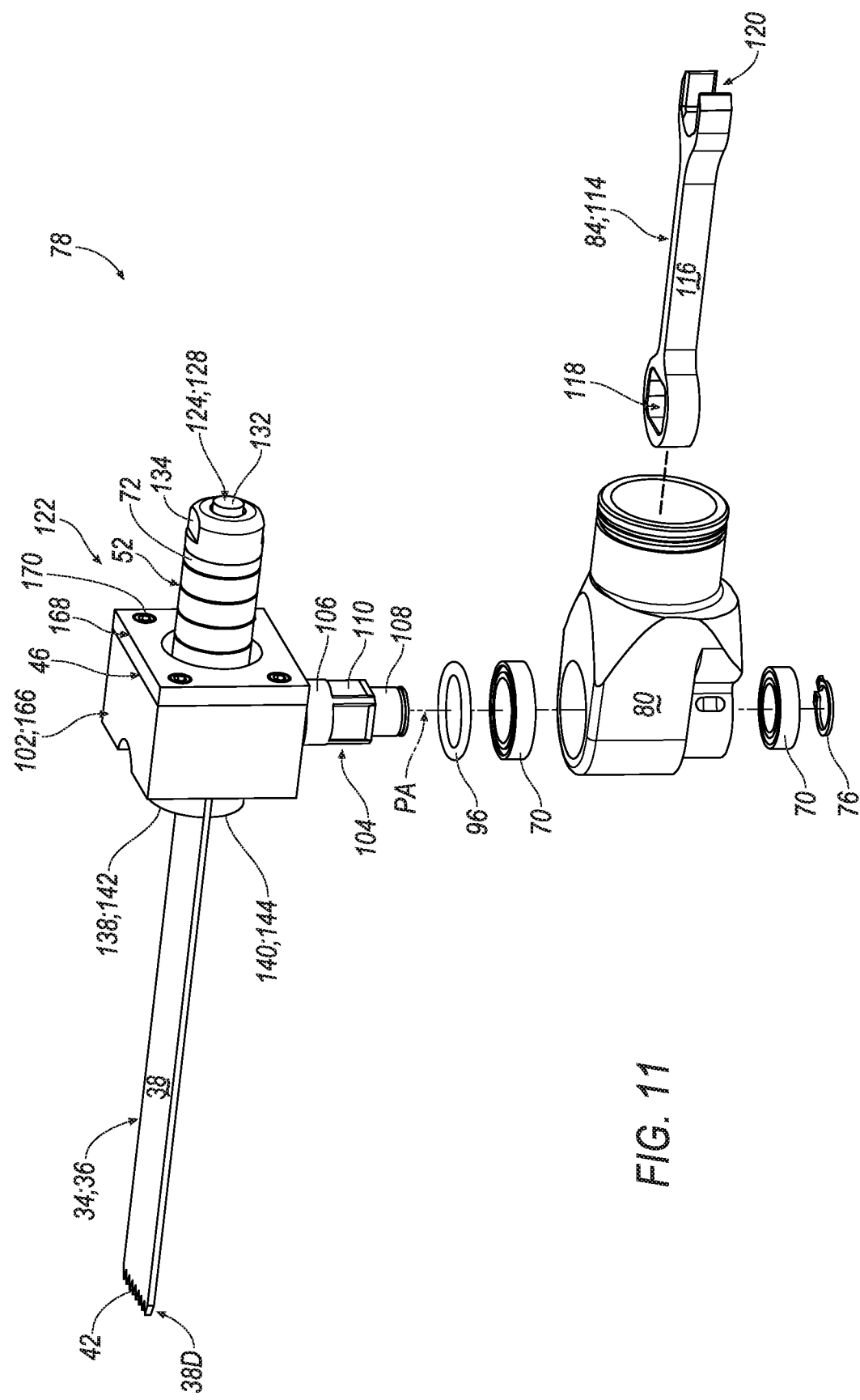
FIG. 11 is a partial, exploded perspective view of the head subassembly of FIG. 10, shown with the carrier, the ultrasonic transducer, and the saw blade spaced from the head body.
Figure 12:
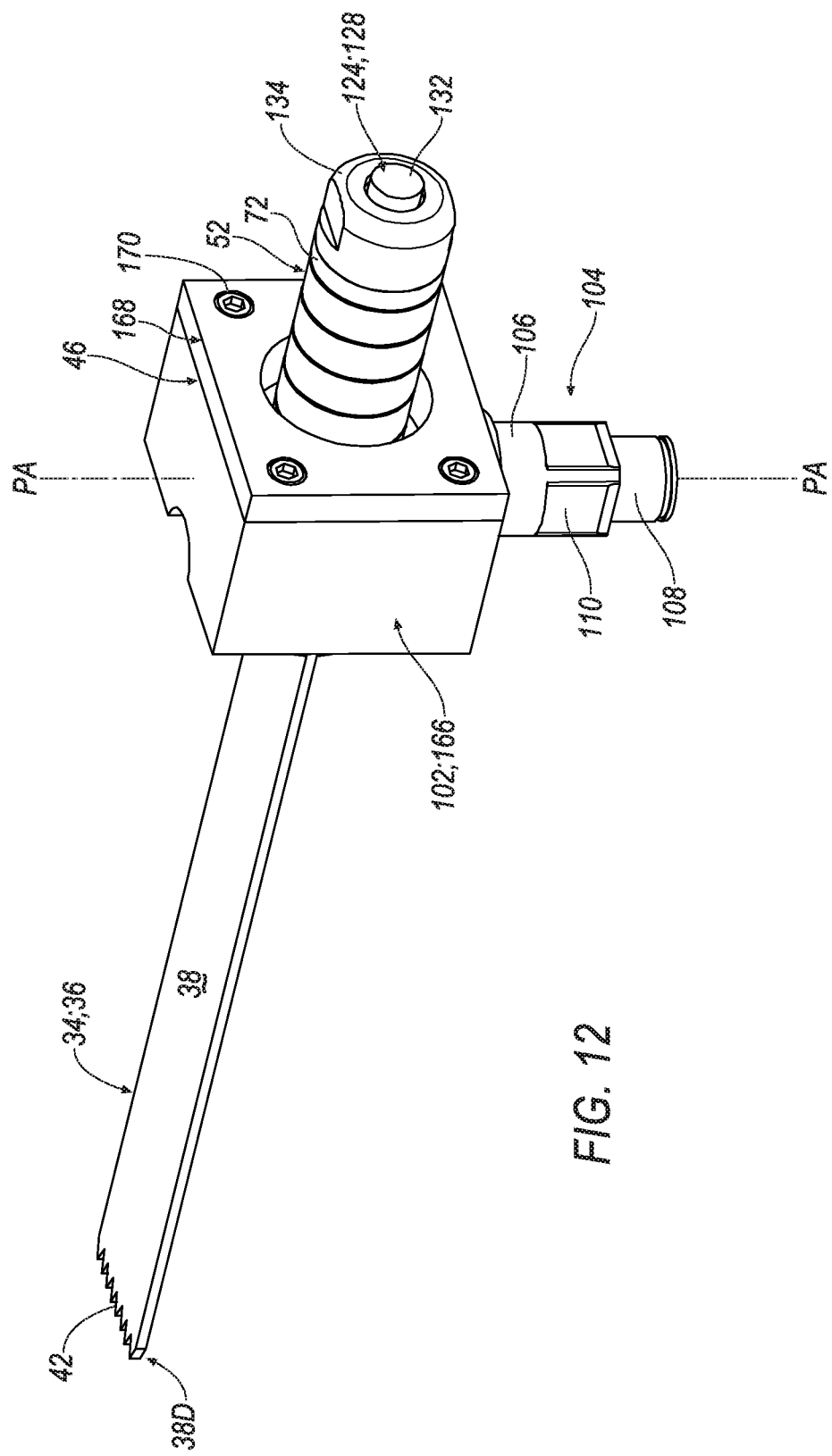
FIG. 12 is a perspective view of the carrier, the ultrasonic transducer, and the saw blade of FIG. 11.
Figure 13:
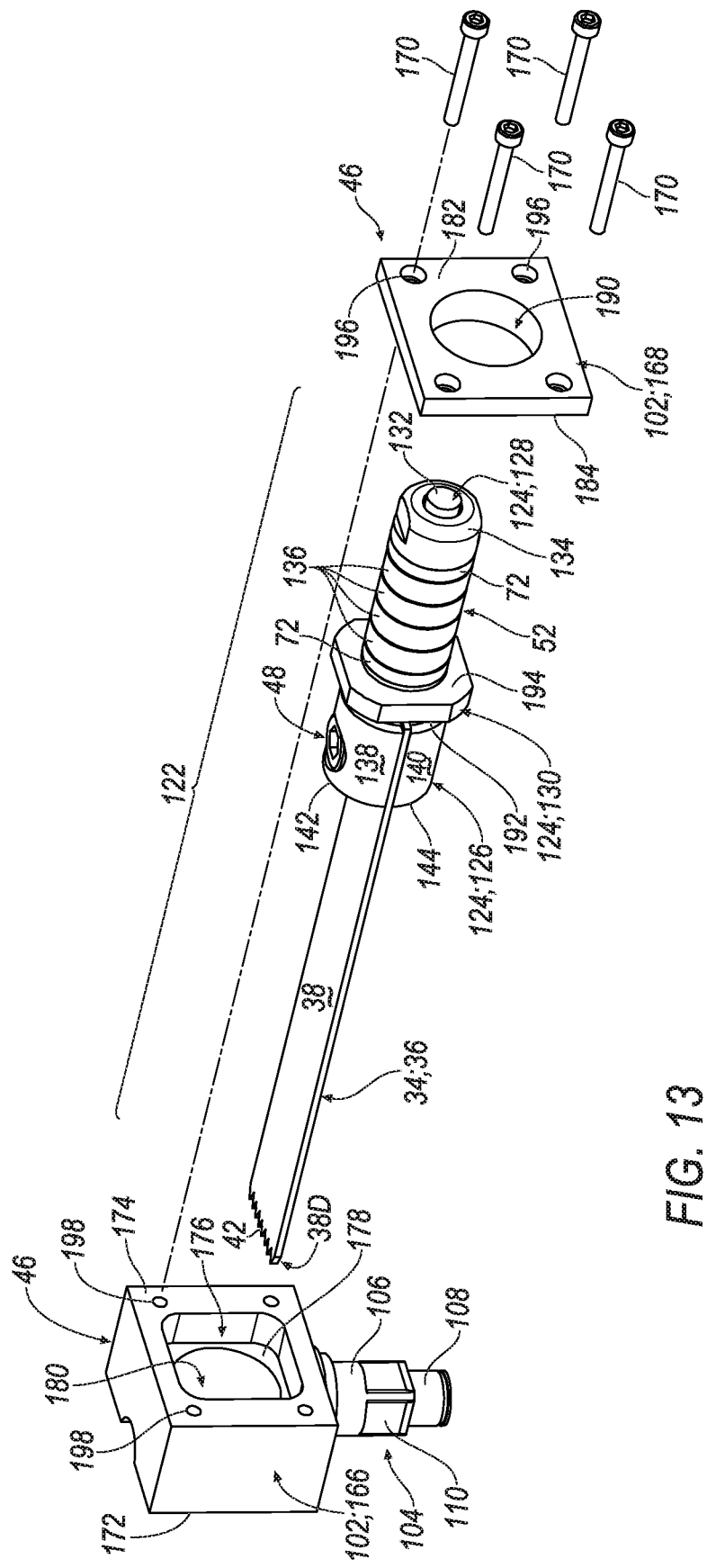
FIG. 13 is a partially-exploded perspective view of the carrier, the ultrasonic transducer, and the saw blade of FIG. 12, the carrier shown comprising a pivot housing and a cover plate spaced from a waveguide subassembly comprising the retainer, the ultrasonic transducer, and a waveguide body.
Figure 14:
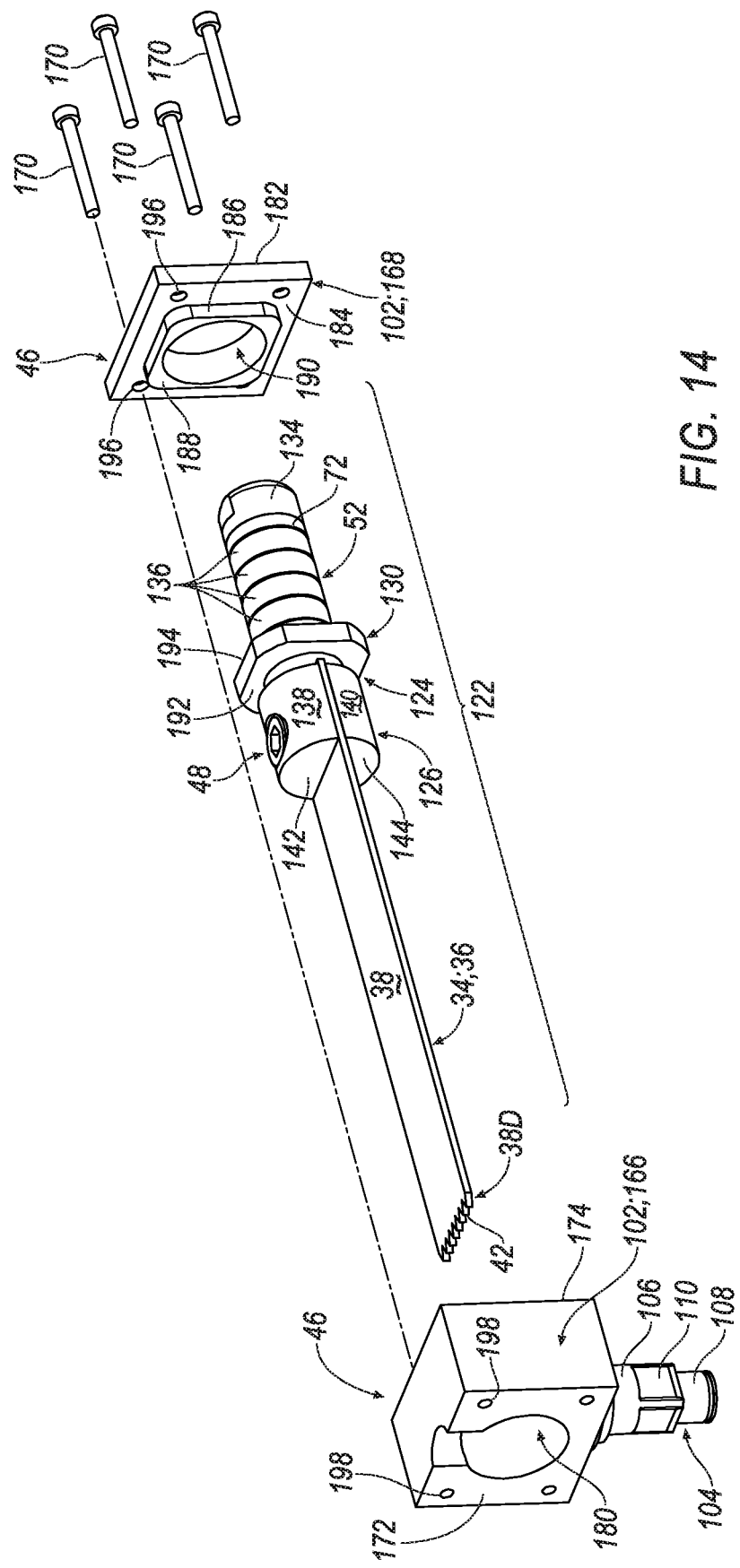
FIG. 14 is another partially-exploded perspective view of the carrier, the ultrasonic transducer, and the saw blade of FIG. 13, shown with the pivot housing and the cover plate spaced from the waveguide subassembly.

With reference to FIGS. 11-14, the carrier 46 of the surgical tool 32 generally comprises a pivot housing 102 and a pivot shaft 104 in the illustrated embodiment. As will be appreciated from the subsequent description below, the pivot housing 102 is coupled to or otherwise formed integrally with the pivot shaft 104, and supports the retainer 48 for concurrent oscillating movement with the saw blade 36 about the pivot axis PA in the first mode M1. As is best shown in FIG. 11, the pivot shaft 104 defines the pivot axis PA in the illustrated embodiment, and comprises a first cylindrical region 106, a second cylindrical region 108, and an interface region 110 disposed between the first cylindrical region 106 and the second cylindrical region 108. Bearings 70 disposed in the head body 80 provide rotational support to the first cylindrical region 106 and the second cylindrical region 108 of the pivot shaft 104 to facilitate oscillating movement of the carrier 46 about the pivot axis PA (see also FIG. 5). One or more seals 96 and/or other components (e.g., o-rings, caps, covers, and the like) may be provided to seal the bearings 70 supported within the head body 80 from exposure to the outside environment. A circlip 76, disposed within in a slot (not shown in detail) formed in the second cylindrical region 108 of the pivot shaft 104, restricts axial movement of the carrier 46 relative to the head body 80. It will be appreciated that the head body 80 could be configured to support the carrier 46 for oscillating movement about the pivot axis PA relative to the handpiece body 44 in ways, such as with different arrangements of bearings 70, circlips 76, and the like, without departing from the scope of the present disclosure Referring now to FIGS. 4 and 7-14, as noted above, the linkage 84 forms part of the head subassembly 78 in the illustrated embodiment, and translates rotational torque generated by the motor 60 about the motor axis MA into oscillating movement of the carrier 46, the retainer 48, and the saw blade 36 about the pivot axis PA in the first mode M1 (see also FIGS. 17A-17C). The linkage 84 is interposed in force-translating relation between the motor 60 and the carrier 46. More specifically, in the illustrated embodiment, the output shaft 68 of the motor 60 comprises an eccentric head 112 which is arranged for orbital motion about the motor axis MA (see also FIGS. 17A-17C), and the linkage 84 comprises a connecting rod 114 interposed between the pivot shaft 104 of the carrier 46 and the eccentric head 112.

Figure 5:
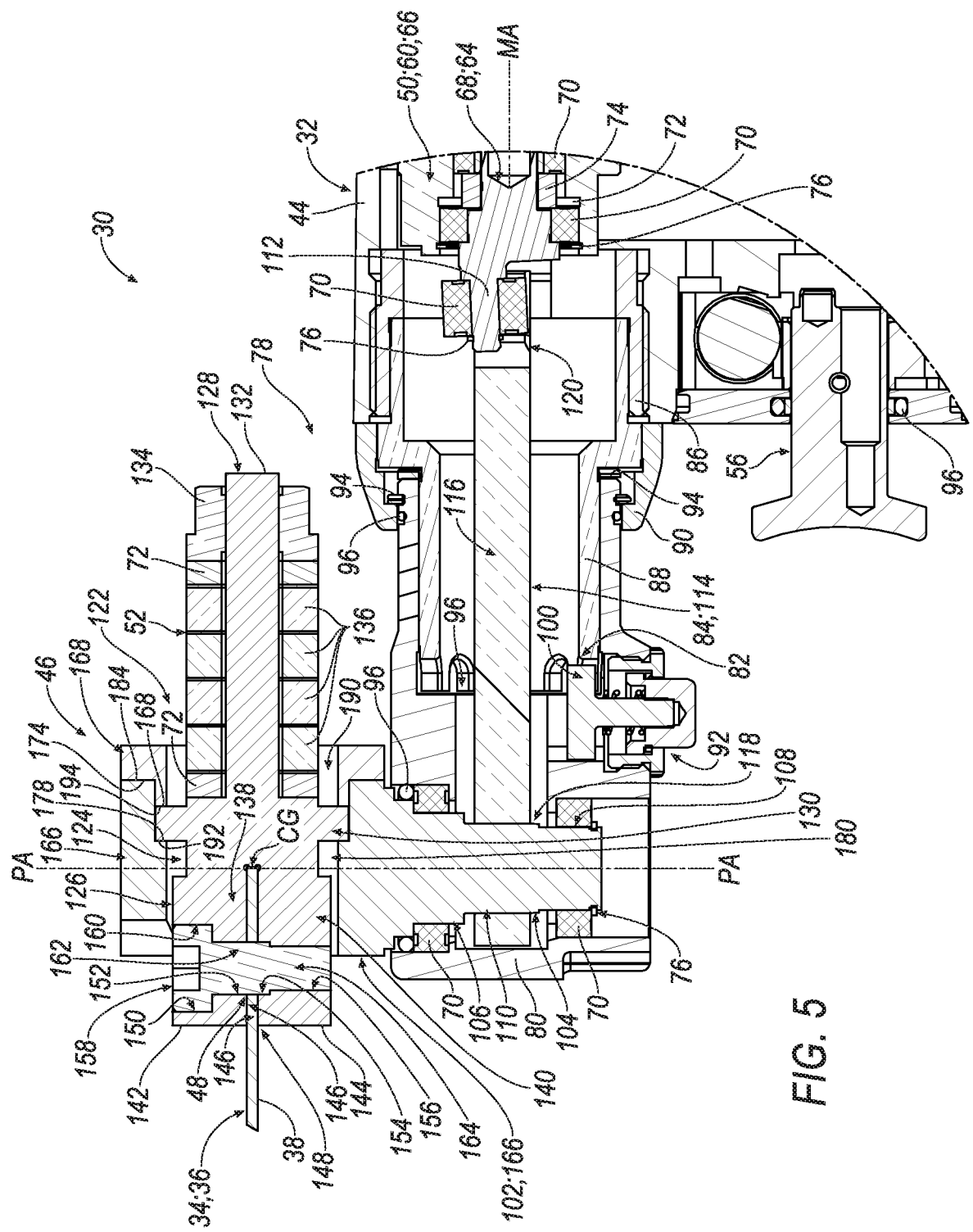
FIG. 5 is an enlarged, partial sectional view taken along indicia 5 in FIG. 4.

The connecting rod 114 of the linkage 84 comprises a rod body 116 which extends between a socket portion 118 and a fork portion 120 (see FIG. 11). The socket portion 118 is shaped to receive and move concurrently with the interface region 110 of the pivot shaft 104 of the carrier 46. In the illustrated embodiment, both the interface region 110 and the socket portion 118 are provided with generally rounded-rectangular profiles which interlock or otherwise abut to limit relative movement from occurring between the connecting rod 114 and the pivot shaft 104. The fork portion 120 of the connecting rod 114 is shaped to engage the eccentric head 112 of the output shaft 68 of the motor 60. More specifically, as shown in FIG. 5, a bearing 70 is supported on the eccentric head 112 of the output shaft 68 and remains in contact with the fork portion 120 of the connecting rod 114 such that rotation of the output shaft 68 about the motor axis MA causes the fork portion 120 of the connecting rod 114 to articulate relative to the pivot axis PA which, in turn, effects oscillating movement of the carrier 46 about the pivot axis PA (see also FIGS. 17A-17C). Those having ordinary skill in the art will appreciate that the linkage 84 could be configured in a number of different ways sufficient to translate rotation about the motor axis MA into oscillating movement about the pivot axis PA. Furthermore, and as will be appreciated from the subsequent description below, it is conceivable that the surgical tool 32 could effect oscillating movement in the first mode M1 without the use of a discrete linkage 84 in some embodiments.

In the illustrated embodiment, the various components of the head subassembly 78 are generally configured such that the pivot axis PA is arranged substantially perpendicular to the motor axis MA and is substantially normal to the sagittal plane SP (see FIG. 4). However, other arrangements are contemplated by the present disclosure, and it will be appreciated that the head subassembly 78 could be configured in a number of different ways sufficient to effect oscillation of the carrier 46 about the pivot axis PA relative to the handpiece body 44, with or without the use of a discrete head body 80, indexing mechanism 82, and/or linkage 84. Furthermore, it is conceivable that the pivot axis PA could be arranged in other ways relative to the motor axis MA and/or the sagittal plane SP in some embodiments. By way of non-limiting example, the pivot axis PA could be arranged to intersect the sagittal plane SP at an angle (not shown). Other configurations are contemplated.

Those having ordinary skill in the art will appreciate that the surgical tool 32 could be configured to facilitate oscillation of the carrier 46 about the pivot axis PA via the actuator 50 in ways other than via the various components of the head subassembly 78 described above and illustrated throughout the drawings. More specifically, while head subassembly 78 is provided with the connecting rod 114 as the linkage 84 in the illustrated embodiment to translate rotation about the motor axis MA into oscillating movement about the pivot axis PA, it will be appreciated that the linkage 84 could be configured to translate rotation into oscillation in other ways, such as via an arrangement of gears (not shown). Moreover, it is conceivable that the surgical tool 32 could omit the linkage 84 and/or the head subassembly 78 in some embodiments. By way non-limiting example, the actuator 50 could be configured as a "reversing motor" which directly generates an oscillating output to move the carrier 46 back and forth about the pivot axis PA without the use of a linkage 84 of the type described herein. Other configurations are contemplated.

Referring now to FIGS. 4-5, as noted above, the surgical tool 32 is provided with the ultrasonic transducer 52 to facilitate movement in the second mode M2 by selectively generating ultrasonic energy which resonates the saw blade 36 such that the teeth 42 at the distal blade end 38D reciprocate proximally and distally within the sagittal plane SP (see also FIGS. 17A-20). To this end, the surgical tool 32 of the illustrated embodiment is provided with a waveguide subassembly, generally indicated at 122 (see FIGS. 13-16). As will be appreciated from the subsequent description below, the waveguide subassembly 122 includes or is otherwise defined by the various components which are operatively attached to the carrier 46 for concurrent oscillating movement about the pivot axis PA in the first mode M1, such as the blade body 38, the retainer 48, and the ultrasonic transducer 52. In addition to these components, the waveguide subassembly 122 also includes a waveguide body, generally indicated at 124. As is described in greater detail below, the waveguide body 124 is interposed in force-translating relation between the retainer 48 and the ultrasonic transducer 52 and helps direct ultrasonic energy generated by the ultrasonic transducer 52 toward the distal blade end 38D of the saw blade 36 to facilitate reciprocating movement in the second mode M2.

Figure 15:
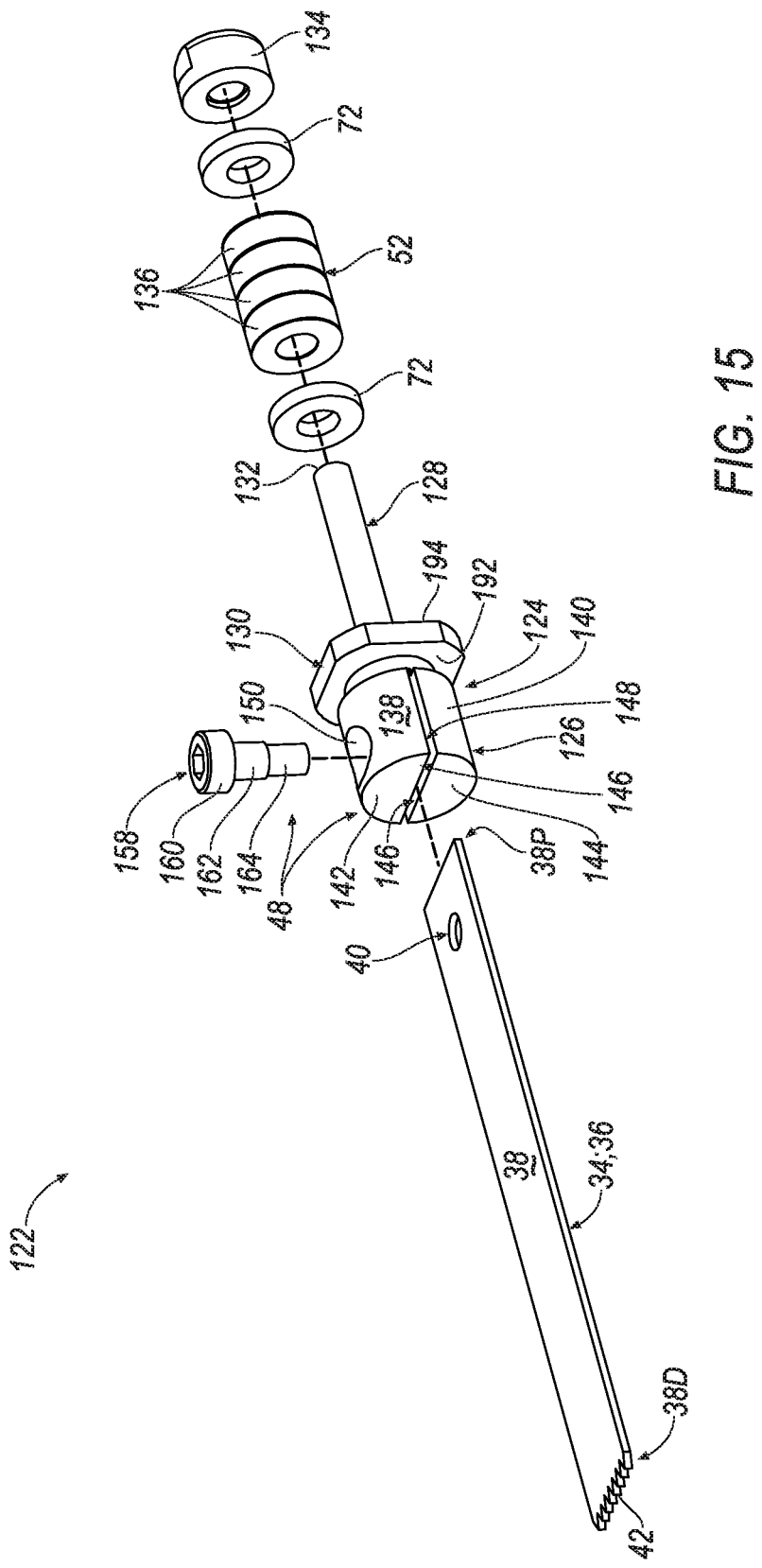
FIG. 15 is an exploded perspective view of the waveguide subassembly of FIGS. 14-15, shown with the ultrasonic transducer and the saw blade spaced from the waveguide body.
Figure 16:
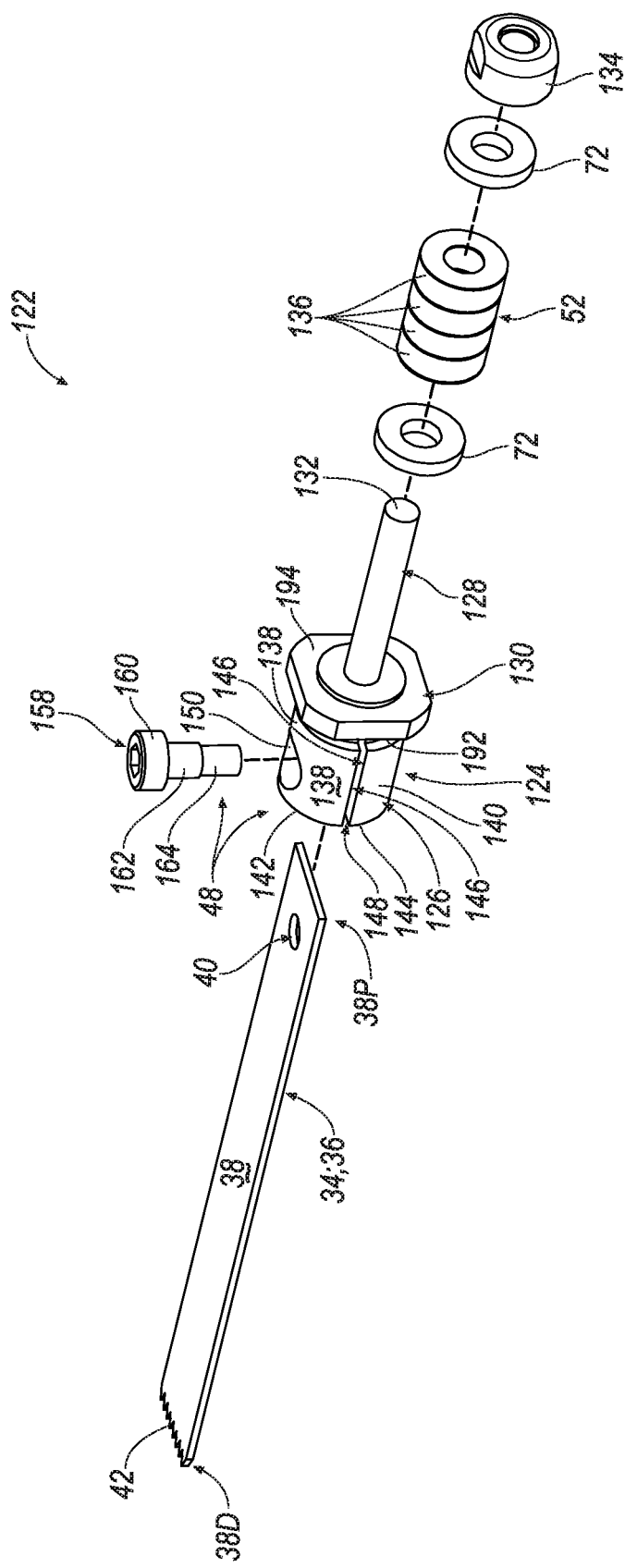
FIG. 16 is another exploded perspective view of the waveguide subassembly of FIG. 15.
Figure 17A:
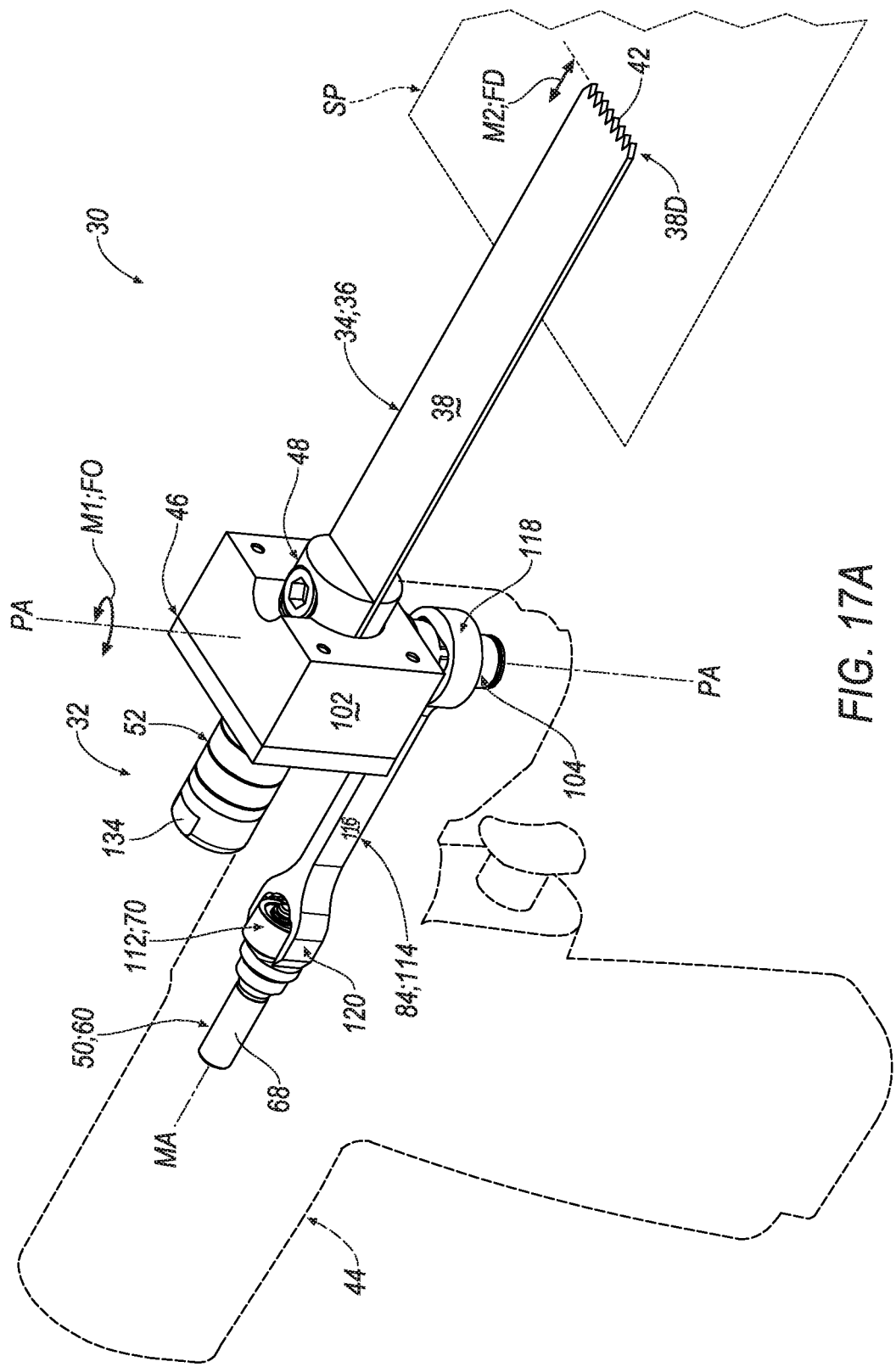
FIG. 17A is a partial perspective view of the surgical system of FIGS. 1-5, shown with the saw blade positioned within the sagittal plane.
Figure 17B:
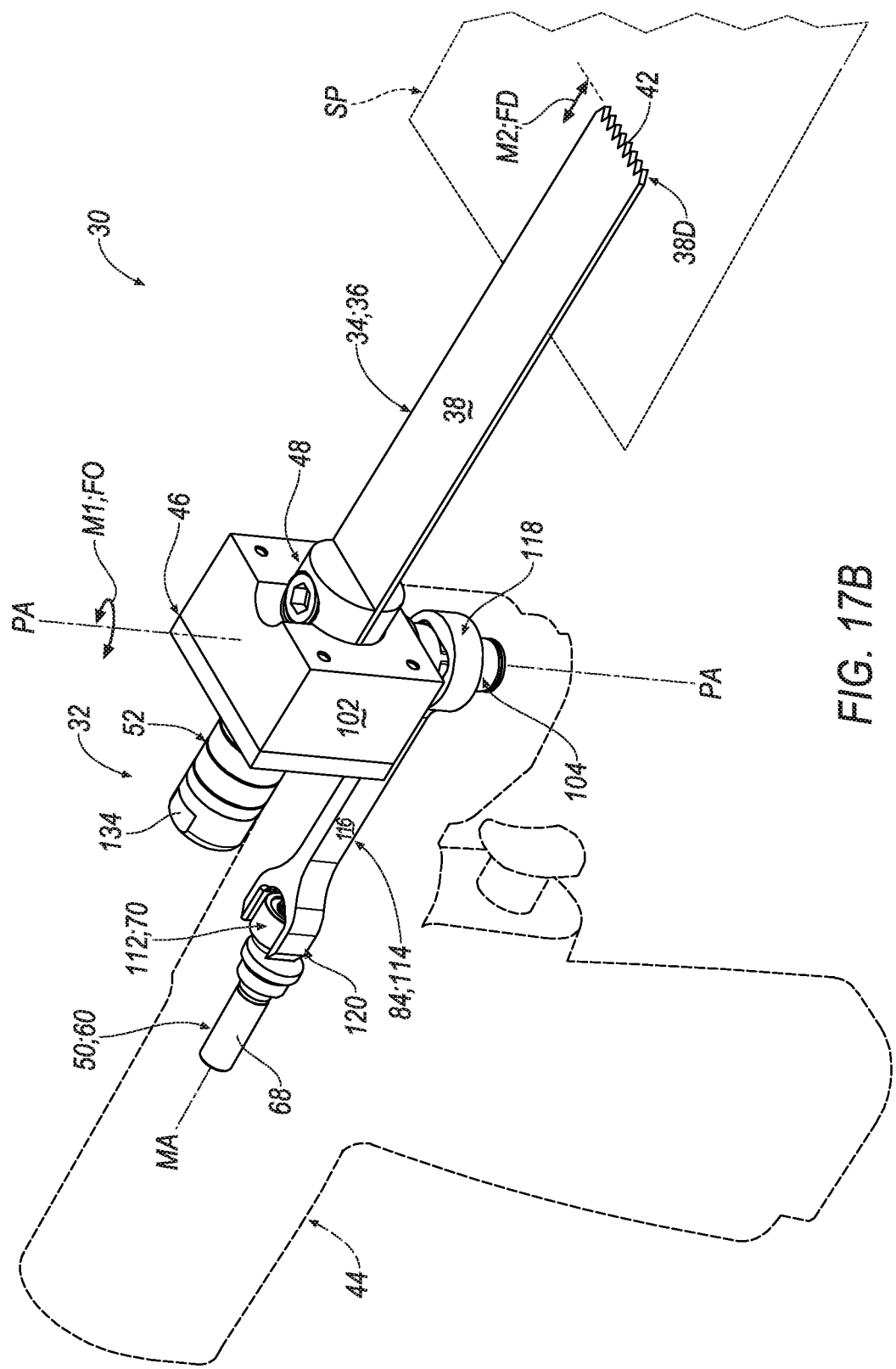
FIG. 17B is another partial perspective view of the surgical system of FIG. 17A, shown with the saw blade pivoted in a first direction about the pivot axis.
Figure 17C:
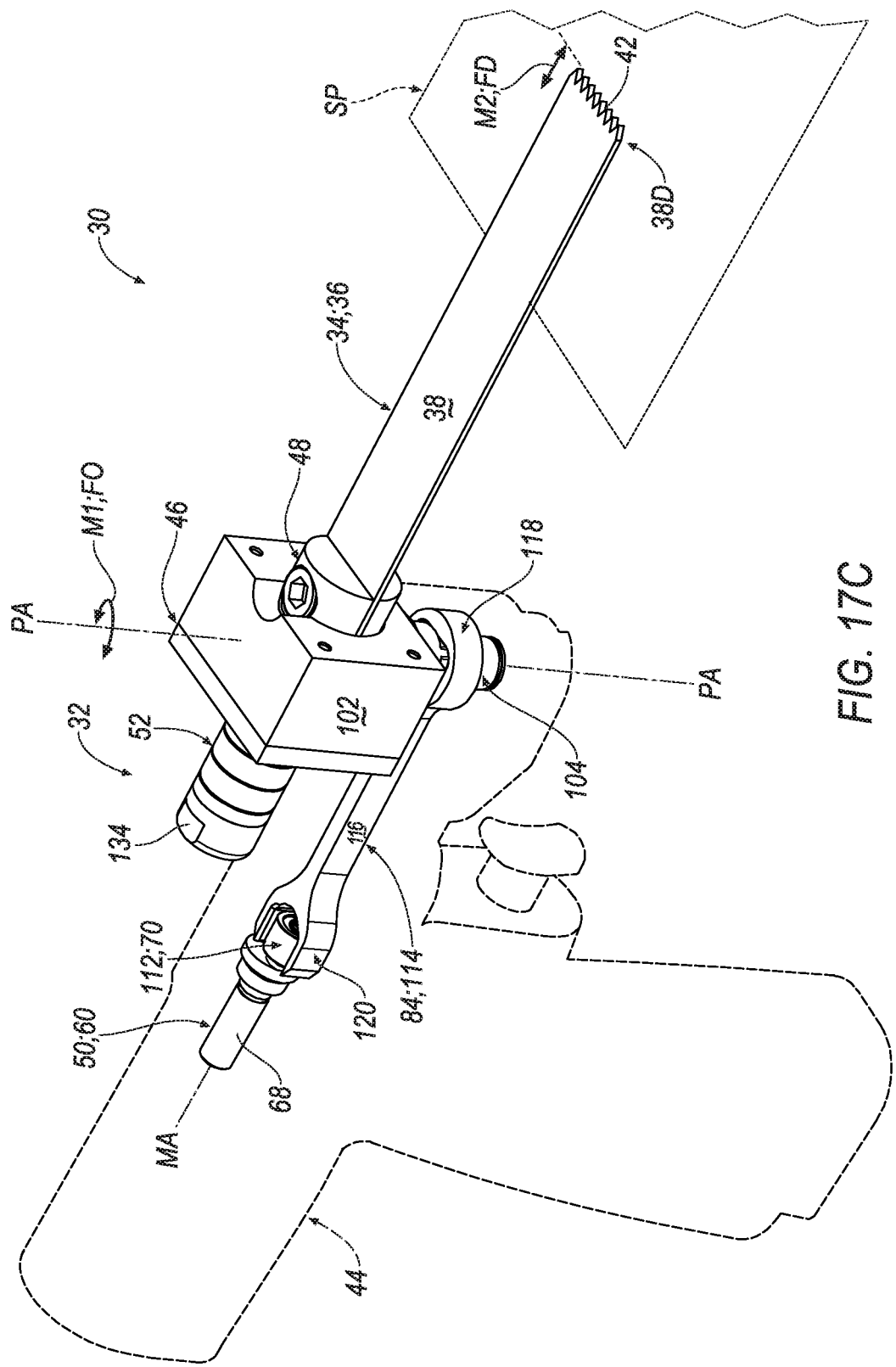
FIG. 17C is another partial perspective view of the surgical system of FIGS. 17A-17B, shown with the saw blade pivoted in a second direction about the pivot axis.

As is best shown in FIGS. 5 and 15-16, the waveguide body 124 is formed as a unitary, one-piece component having a retainer portion 126, a mount portion 128, and a flange portion 130. The flange portion 130 is arranged between the retainer portion 126 and the mount portion 128, and is operatively attached to the carrier 46 as described in greater detail below. The mount portion 128 is configured to secure the ultrasonic transducer 52 to the waveguide body 124, and has a substantially cylindrical profile extending from the flange portion 130 to a proximal mount end 132. The proximal mount end 132 of the mount portion 128 may be disposed in threaded engagement (not shown) with a backnut 134 to secure the ultrasonic transducer 52 to the waveguide body 124.

In the illustrated embodiment, the ultrasonic transducer 52 comprises a "stack" of four piezoelectric transducers 136 which are arranged between washers 72 which respectively abut the backnut 134 and the flange portion 130 of the waveguide body 124. Here, when the backnut 134 is secured to the mount portion 128 (e.g., by applying toque to the threaded engagement), the piezoelectric transducers 136 are effectively compressed in engagement against each other and also against the flange portion 130 and the backnut 134. Different arrangements of piezoelectric transducers 136 are contemplated by the present disclosure, and may be disposed in direct contact with the flange portion 130 of the waveguide body 124 in some embodiments (e.g., without the use of washers 72). Moreover, it will be appreciated that the ultrasonic transducer 52 could employ different quantities of piezoelectric transducers 136, of the same configuration or of different configurations, which are arranged, wired, and/or driven by the controller 58 in any suitable way sufficient to facilitate the reciprocating movement in the second mode M2 described above. In addition, while the backnut 134 and the mount portion 128 cooperate to secure the ultrasonic transducer 52 to the waveguide body 124 in the illustrated embodiment, it will be appreciated that other configurations are contemplated. By way of non-limiting example, a bolt (not shown) could extend through the annular piezoelectric transducers 136 and into threaded engagement with a tapped hole formed in the waveguide body (not shown). Furthermore, those having ordinary skill in the art will appreciate that other types of transducers 52 may be utilized in certain embodiments, including transducers 52 (or actuators) which generate rotational, percussive, and/or translational movement in the second mode M2 superimposed over movement in the first mode M1 without necessarily generating ultrasonic energy. Other configurations are contemplated.

As shown in FIGS. 15-16, the retainer portion 126 of the waveguide body 124 may comprise first and second brace elements 138, 140 which extend away from the flange portion 130 to respective first and second brace ends 142, 144. The first and second brace elements 138, 140 may each comprise a respective, generally, i.e., substantially, planar brace surface 146 arranged substantially parallel to and spaced from the sagittal plane SP. The brace surfaces 146 face towards each other and define a slot 148 therebetween. The slot 148 is shaped to receive the proximal blade end 38P and a portion of the blade body 38 of the saw blade 36.

As is best shown in FIG. 5, the first brace element 138 comprises a head boss 150 and a first shank boss 152, and the second brace element 140 comprises a second shank boss 154 and an engagement boss 156. Here, a shoulder bolt 158 (see also FIG. 2) is provided to secure the saw blade 36 to the retainer 48 by "pinching" the blade body 38 against and between the brace surfaces 146 of the first and second brace elements 138, 140. To this end, the shoulder bolt 158 generally comprises a head 160, a shank 162, and a tail 164 (see FIGS. 15-16). The head 160 of the shoulder bolt 158 is shaped to be received within the head boss 150 formed in the first brace element 138. The shank 162 of the shoulder bolt 158 is shaped to be received within the first shank boss 152 formed in the first brace element 138, within the retention mount 40 formed in the blade body 38 of the saw blade 36, and also within the second shank boss 154 formed in the second brace element 140. The tail 164 of the shoulder bolt 158 is shaped to be received within the engagement boss 156 formed in the second brace element 140, such as via threaded engagement (not shown). Other configurations of the brace elements 138, 140, the shoulder bolt 158, and/or the retainer 48 are contemplated.

It will be appreciated that radial abutment of the shank 162 of the shoulder bolt 158 against the retention mount 40 of the saw blade 36, combined with planar abutment of the brace surfaces 146 of the first and second brace elements 138, 140 against the blade body 38 of the saw blade 36, effectively prevents relative movement from occurring between the saw blade 36 and the waveguide body 124 when the shoulder bolt 158 is "tightened" to compress the saw blade 36 between the first and second brace elements 138, 140. Thus, in the illustrated embodiment, the retainer 48 of the surgical tool 32 is realized by the shank 162 of the shoulder bolt 158 and the respective brace surfaces 146 of the first and second brace elements 138, 140 of the retainer portion 126 of the waveguide body 124. However, those having ordinary skill in the art will appreciate that the retainer 48 could be configured in a number of different ways sufficient to facilitate releasably attaching the saw blade 36 to the carrier 46 for concurrent oscillating movement about the pivot axis PA within the sagittal plane SP. By way of non-limiting example, rather than employing the shoulder bolt 158 described above as a part of the retainer 48, it is conceivable that the retainer 48 could be provided with a lever-actuated locking mechanism (not shown) to facilitate releasably attaching the saw blade 36 to the carrier 46 for concurrent oscillating movement about the pivot axis PA. Other configurations are contemplated.

As noted above, the illustrated embodiment of the surgical system 30 employs the waveguide subassembly 122 to, among other things, facilitate concurrent oscillating movement of the retainer 48 and the saw blade 36 with the carrier 46 about the pivot axis PA. In order to facilitate attaching the waveguide subassembly 122 to the carrier 46, the pivot housing 102 of the carrier 46 generally comprises a pivot body 166, a cover plate 168, and one or more fasteners 170 which cooperate to removably secure the waveguide subassembly 122 between the pivot body 166 and the cover plate 168 for concurrent oscillating movement about the pivot axis PA in the first mode M1.

Referring now to FIGS. 13-16, the pivot body 166 of the pivot housing 102 comprises a first body face 172 and an opposing second body face 174. A pocket 176 (see FIG. 13) is formed extending from the second body face 174 to a pocket surface 178, and a body bore 180 is formed extending between the pocket surface 178 and the first body face 172. The cover plate 168 of the pivot housing 102 comprises a first cover face 182 and an opposing second cover face 184. A projection 186 (see FIG. 14) is formed extending from the second cover face 184 to a projection surface 188, and a cover bore 190 is formed extending between the projection surface 188 and the first cover face 182. The flange portion 130 of the waveguide body 124 comprises a first flange surface 192 which faces away from the mount portion 128, and a second flange surface 194 which faces away from the retainer portion 126.

As is best shown in FIG. 5, the flange portion 130 of the waveguide body 124 is shaped so as to be received within the pocket 176 formed in the pivot body 166 of the pivot housing 102. In the illustrated embodiment, the flange portion 130 of the waveguide body 124, the pocket 176 of the pivot body 166, and the projection 186 of the cover plate 168 each have correspondingly-shaped, generally rounded rectangular profiles. When the cover plate 168 is secured to the pivot body 166 with the fasteners 170, the second cover face 184 of the cover plate 168 abuts the second body face 174 of the pivot body 166, the pocket surface 178 of the pivot body 166 abuts the first flange surface 192 of the waveguide body 124, and the projection surface 188 of the cover plate 168 abuts the second flange surface 194 of the waveguide body 124. To this end, cover holes 196 are formed between the first and second cover faces 182, 184 of the cover plate 168 to receive respective fasteners 170 which each extend into threaded engagement (not shown) with respective body holes 198 formed between the first and second body faces 172, 174 of the pivot body 166.

With continued reference to FIG. 5, in one embodiment, the body bore 180 of the pivot body 166 accommodates but does not contact the retainer portion 126 of the waveguide body 124, the shoulder bolt 158, or any portion of the saw blade 36 when the cover plate 168 secured to the pivot body 166 with the fasteners 170 to assemble the pivot housing 102 of the carrier 46. Similarly, the cover bore 190 of the cover plate 168 accommodates but does not contact the mount portion 128 of the waveguide body 124 or any portion of the ultrasonic transducer 52, the backnut 134, or the washers 72 supported along the mount portion 128. This configuration helps ensure that ultrasonic energy generated by the ultrasonic transducer 52 is efficiently directed toward the distal blade end 38D of the saw blade 36 in the illustrated embodiment, rather than toward the handpiece body 44. In the illustrated embodiment, the cover bore 190 and the body bore 180 each have cylindrical profiles, and the first and second brace elements 138, 140 of the retainer portion 126 of the waveguide body 124 each have generally semicylindrical profiles. However, it will be appreciated that other configurations are contemplated.

In some embodiments, the flange portion 130 of the waveguide body 124 is arranged closer to the pivot axis PA than the mount portion 128. Put differently, the flange portion 130 which contacts the carrier 46 is closer to the pivot axis PA than the ultrasonic transducer 52. As will be appreciated from the subsequent description below in connection with FIGS. 19-21, this configuration helps prevent ultrasonic energy generated by the ultrasonic transducer 52 from propagating toward the handpiece body 44 because of the specific configuration of the waveguide subassembly 122.

As shown in FIG. 5, the pocket surface 178 of the pivot body 166 of the pivot housing 102 of the carrier 46 is spaced from the pivot axis PA in the illustrated embodiment. This arrangement positions the waveguide subassembly 122 such that its center of gravity CG falls along or in close proximity to the pivot axis PA, which contributes to improved performance of the surgical tool 32 during use. More specifically, this arrangement helps prevent the occurrence of disadvantageous inertial forces that could otherwise translate to the handpiece body 44 if the center of gravity CG of the waveguide subassembly 122 were spaced at a relatively large distance from the pivot axis PA. Nevertheless, it will be appreciated that the one or more components of the carrier 46 and/or the waveguide subassembly 122 could be configured and/or arranged in other ways sufficient position the center of gravity CG of the waveguide subassembly 122 (and/or of the carrier 46) along or in close proximity to the pivot axis PA in order to promote advantageous oscillating balance.

Figure 6B:
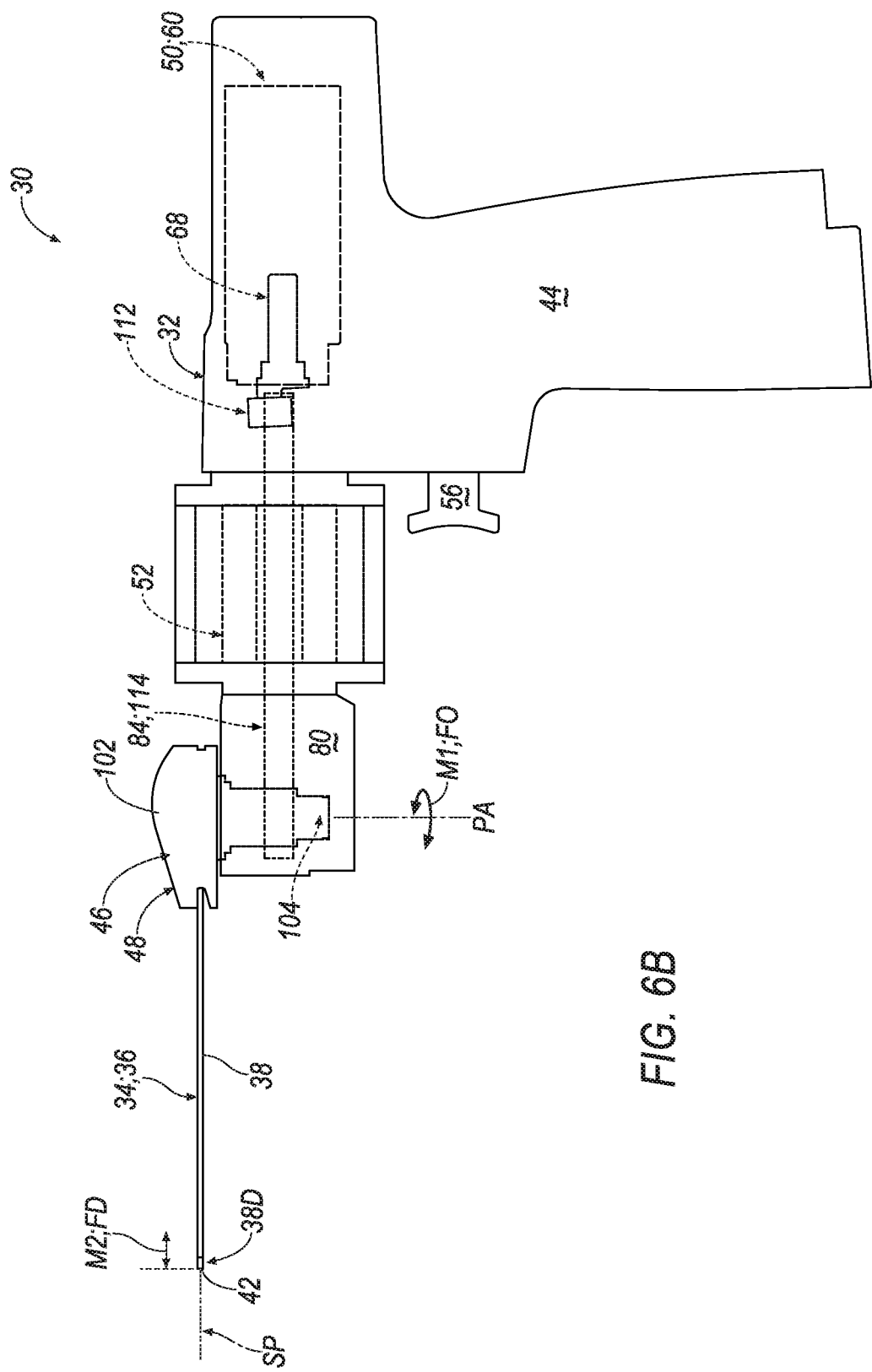
FIG. 6B is a schematic view of another embodiment of a surgical system.

Referring now to FIG. 6A, the illustrated embodiment of the surgical system 30 employs the pivot housing 102 of the carrier 46 to secure the waveguide subassembly 122 for concurrent oscillating movement about the pivot axis PA, as described above. In this embodiment, because the waveguide subassembly 122 includes the retainer 48 and the ultrasonic transducer 52, it will be appreciated that ultrasonic transducer 52 is operatively attached to the handpiece body 44 and, more specifically, is also coupled to the carrier 46 for concurrent oscillating movement about the pivot axis PA. However, the ultrasonic transducer 52 could be operatively attached to the handpiece body 44 in other ways sufficient to facilitate generate ultrasonic energy to resonate the saw blade 36 and thereby effect movement in the second mode M2. By way of non-limiting example, and as is depicted schematically in FIG. 6B, the ultrasonic transducer 52 could be interposed between the handpiece body 44 and the head body 80 in some embodiments. Here in the embodiment illustrated in FIG. 6B, the linkage 84 extends through the annular ultrasonic transducer 52, and ultrasonic energy generated by the ultrasonic transducer 52 causes the head body 80 (and, thus, the pivot axis PA) to reciprocate with the saw blade 36 in the second mode M2. It will be appreciated that the other configurations of the surgical tool 32, besides those depicted schematically in FIGS. 6A-6B, are contemplated by the present disclosure.

Figure 18A:
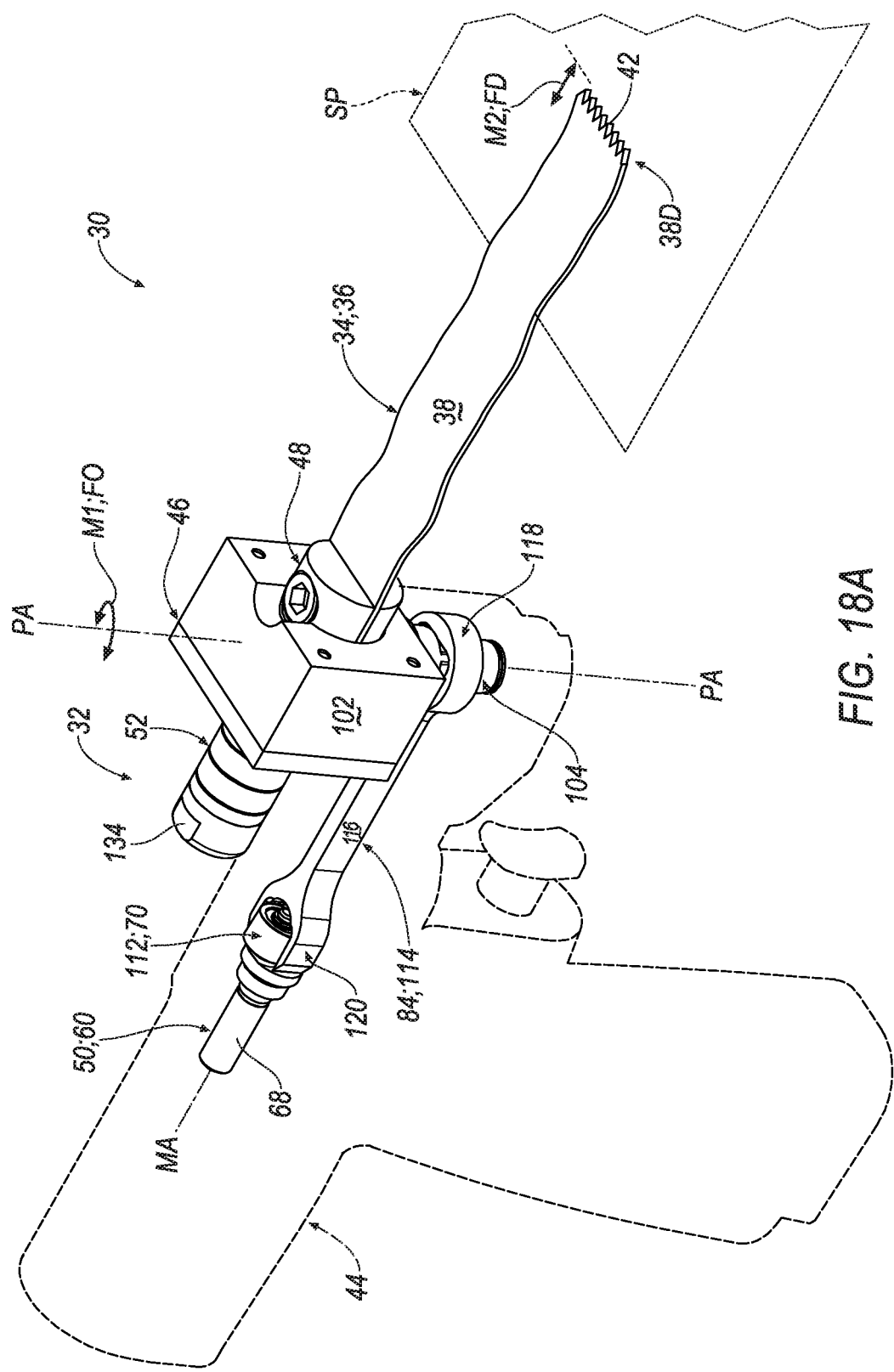
FIG. 18A is another partial perspective view of the surgical system of FIG. 17A, shown with the saw blade positioned within the sagittal plane and illustrated in an exaggerated state of resonance.
Figure 18B:
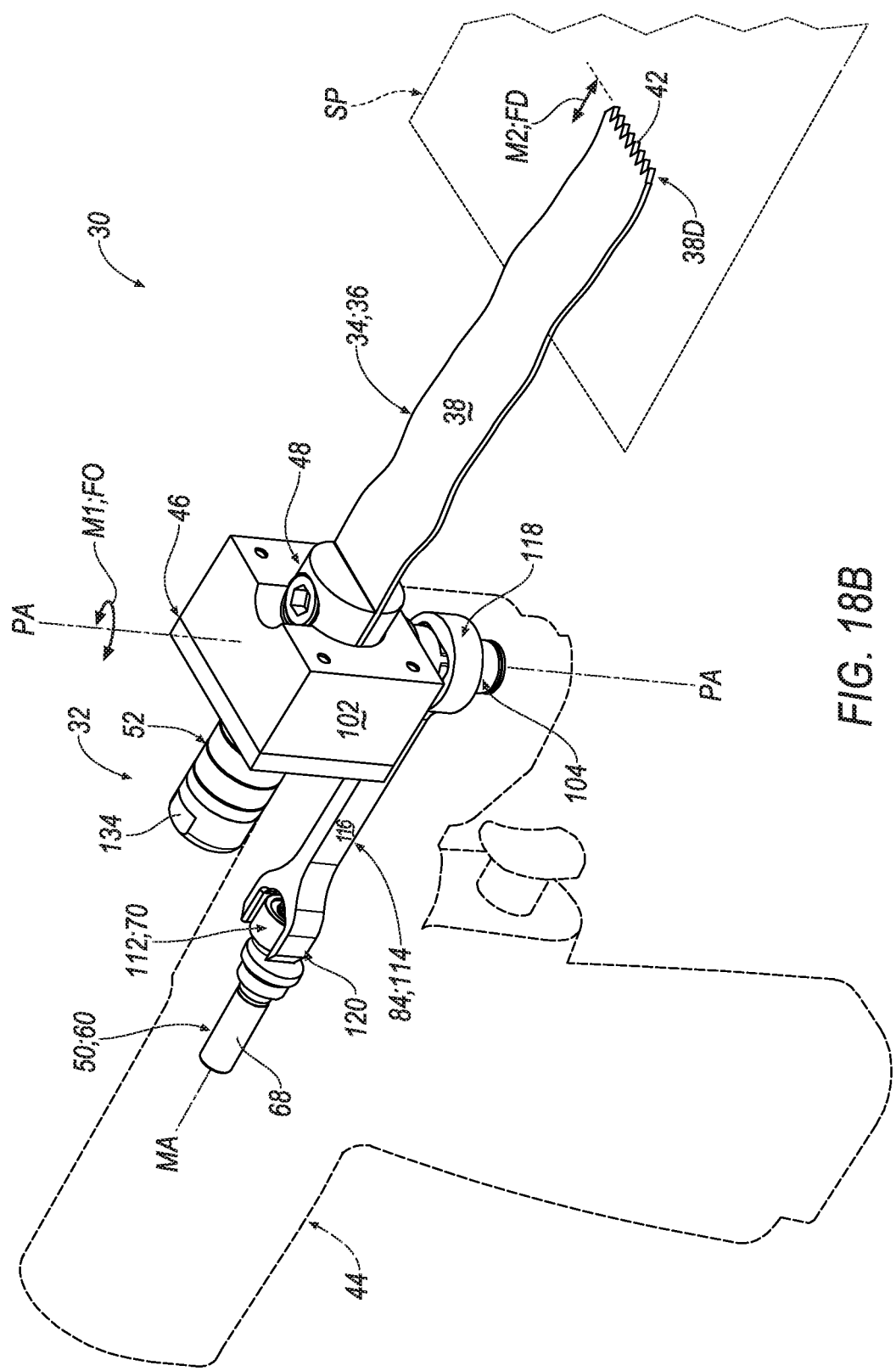
FIG. 18B is another partial perspective view of the surgical system of FIG. 18A, shown with the saw blade pivoted in a first direction about the pivot axis and illustrated in an exaggerated state of resonance.
Figure 18C:
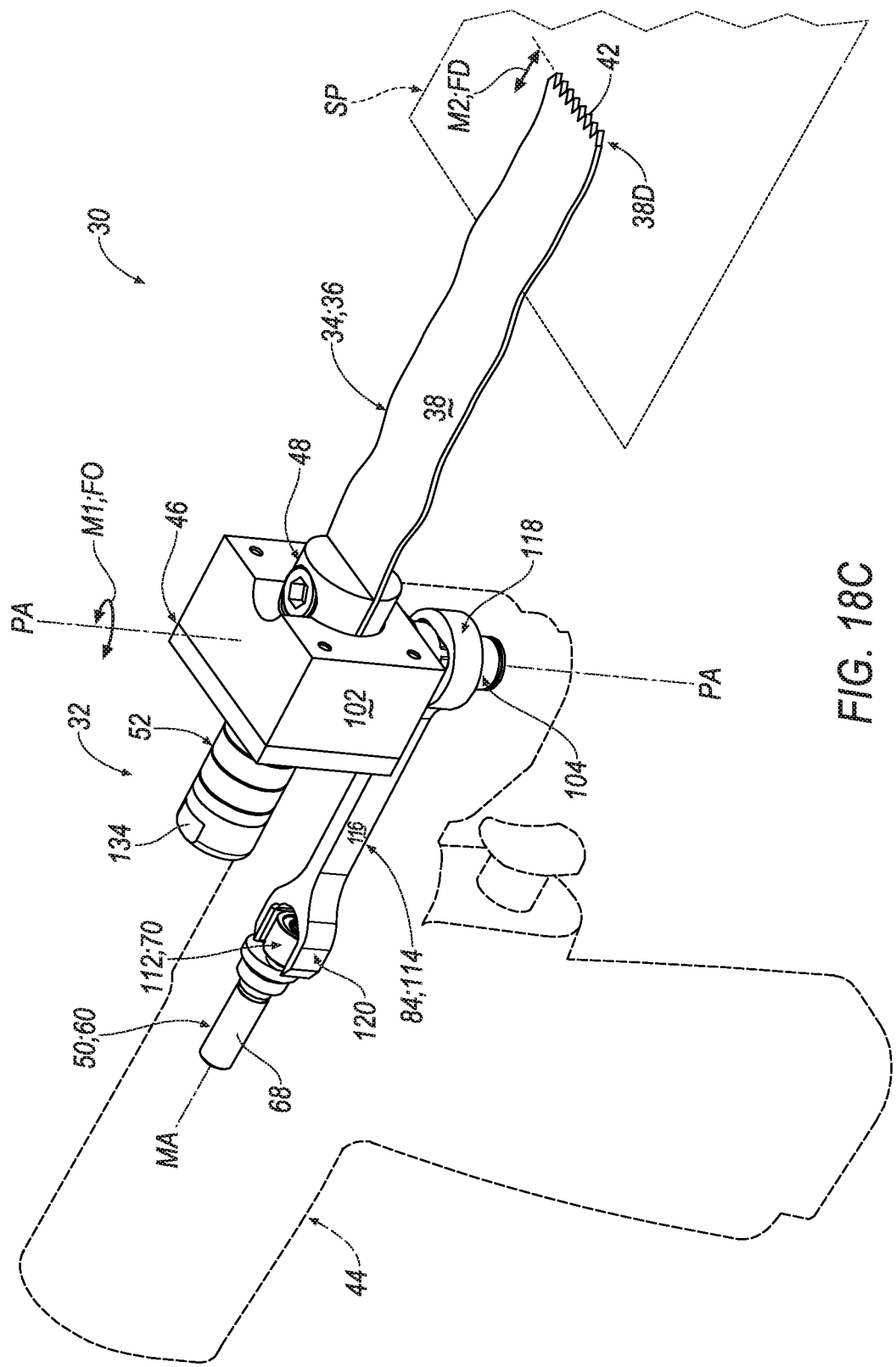
FIG. 18C is another partial perspective view of the surgical system of FIGS. 18A-18B, shown with the saw blade pivoted in a second direction about the pivot axis and illustrated in an exaggerated state of resonance.
Figure 19:
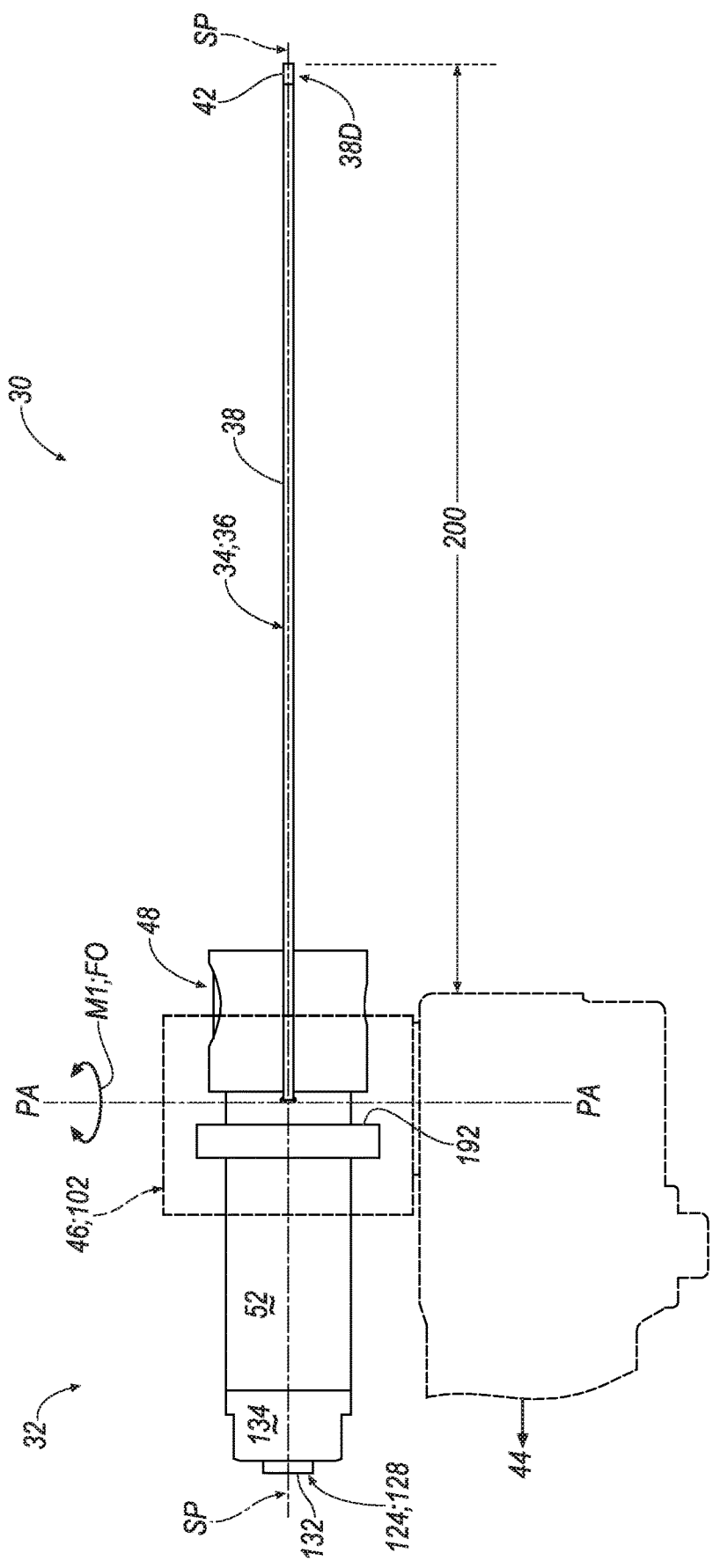
FIG. 19 is a partial, right-side schematic view of the surgical system arranged as depicted in FIG. 17A.

Referring now to FIGS. 17A-21, as noted above, the surgical tool 32 is configured to move the saw blade 36 in: the first mode M1 defined by oscillating movement effected by the actuator 50 which pivots the carrier 46 and the retainer 48 and thereby moves the saw blade 36 back and forth about the pivot axis PA within the sagittal plane SP (compare FIGS. 17A-17C sequentially); and the second mode M2 defined by reciprocating movement effected by the ultrasonic transducer 52 which resonates the saw blade 36 and thereby moves the teeth 42 at the distal blade end 38D proximally and distally within the sagittal plane SP (compare FIGS. 19-20 sequentially; see also FIGS. 18A-18C).

In FIGS. 17A-17C and 19, the saw blade 36 is shown in various positions within the sagittal plane SP, and the blade body 38 is depicted as having a generally rectangular, planar profile extending from the retainer 48 to the teeth 42 arranged adjacent the distal blade end 38D. However, in FIGS. 18A-18C and 20, the saw blade 36 is shown in an exaggerated state of resonance resulting from the generation of ultrasonic energy via the ultrasonic transducer 52. For the purposes of clarity and consistency, while FIGS. 17A-17C and 19 respectively correspond to FIGS. 18A-18C and 20 in terms of the relative positions of the handpiece body 44, the retainer 48, and the carrier 46, only FIGS. 18A-18C and 20 depict the saw blade 36 in an exaggerated state of resonance in order to help illustrate movement in the second mode M2. Furthermore, the exaggerated state of resonance of the saw blade 36 depicted in FIGS. 18A-18C and 20 represents the most proximal position of the teeth 42 relative to the handpiece body 44 during movement in the second mode M2.

In FIG. 19, a static reference distance 200 is shown extending from the most distal portion of the head body 80 to the most distal portion of the teeth 42 of the saw blade 36 which, as noted above, is not depicted in an exaggerated state of resonance in FIG. 19. In FIG. 20, a resonant reference distance 202 is shown extending from the most distal portion of the head body 80 to the most distal portion of the teeth 42 of the saw blade 36 which, as noted above, is depicted in an exaggerated state of resonance in FIG. 20 to represent the most proximal position of the teeth 42 during movement in the second mode M2. With continued reference to FIG. 20, both the static reference distance 200 and the resonant reference distance 202 are shown to help illustrate reciprocation of the saw blade 36 distally and proximally in the sagittal plane SP.

In FIG. 20, the difference between the static reference distance 200 and the resonant reference distance 202 defines a retracted reference distance 204. As noted above, FIG. 20 depicts the most proximal position of the teeth 42 relative to the handpiece body 44 during movement in the second mode M2. As such, the retracted reference distance 204 is equal to half of a reciprocation distance 206 of the saw blade 38, which is likewise depicted in FIG. 20. Put differently, the reciprocation distance 206 is twice the retracted reference distance 204 and represents the full range of motion of the teeth 42 proximally and distally in the second mode M2. It will be appreciated that the retracted reference distance 204 and the reciprocation distance 206 shown in FIG. 20 are both exaggerated for illustrative purposes. During testing of the surgical system 30 illustrated herein, the reciprocation distance 206 was measured using a laser vibrometer at approximately 8 μm. This value is exemplary and non-limiting, and it will be appreciated that the reciprocation distance 206 may vary based on, among other things, the specific configuration of the various components of the surgical system 30. Thus, in some embodiments, the reciprocation distance 206 may be greater than 10 μm. Other configurations are contemplated.

Referring now to FIGS. 20-21, in some embodiments, the waveguide body 124 and the saw blade 36 resonate (see FIG. 20; resonance of waveguide body 124 not shown) to define a standing wave 208 (see FIG. 21) in response to ultrasonic energy generated by the ultrasonic transducer 52. FIG. 21 diagrammatically depicts an exemplary standing wave 208 which propagates toward the distal blade end 38D of the saw blade 36 to facilitate movement in the second mode M2 where the teeth 42 at the distal blade end 38D reciprocate proximally and distally within the sagittal plane SP, as noted above.

For illustrative purposes, FIGS. 20-21 each depict corresponding first, second, third, fourth, and fifth reference lines R1, R2, R3, R4, R5 which are normal to the sagittal plane SP. The first reference line R1 is associated with the most proximal part of the mount portion 128 of the waveguide body 124. The second reference line R2 is associated with contact occurring between the waveguide subassembly 122 and the retainer 48; more specifically, where the pocket surface 178 of the pivot body 166 abuts the first flange surface 192 of the waveguide body 124. The third and fourth reference lines R3, R4 are positioned between the proximal blade end 38P and the distal blade end 38D of the saw blade 36. The fifth reference line R5 is associated with the most distal portion of the teeth 42 of the saw blade 36 during resonance.

With continued reference to FIGS. 20-21, the standing wave 208 shown in FIG. 20 passes through the sagittal plane SP (illustrated as a horizontal dash-dash line) to define first and second nodes 210A, 210B arranged between the ultrasonic transducer 52 and the teeth 42 of the saw blade 36. In the illustrated embodiment, the first node 210A is positioned at the second reference line R2, and the second node 210B is positioned at the fourth reference line R4. Here, the first node 210A is arranged adjacent to the flange portion 130 of the waveguide body 124 so as to at least partially inhibit ultrasonic energy from being transferred from the ultrasonic transducer 52 into the handpiece body 44 via the head body 80. Thus, because the first node 210A of the standing wave 208 is positioned where the pocket surface 178 of the pivot body 166 abuts the first flange surface 192 of the waveguide body 124, ultrasonic energy tends not to transfer into the carrier 46. Put differently, positioning a node of the standing wave 208 where the waveguide body 124 contacts the carrier 46 results in minimal translation of vibration to the handpiece body 44 in some embodiments.

The standing wave 208 depicted in FIG. 21 also defines first, second, and third antinodes 212A, 212B, 212C in the illustrated embodiment. Here, the first antinode 212A is positioned at the first reference line R1, the second antinode 212B is positioned at the third reference line R3, and the third antinode 212C is positioned at the fifth reference line R5. The third antinode 212C is arranged adjacent to the distal blade end 38D of the saw blade 36 during resonance to facilitate reciprocation of the teeth 42 within the sagittal plane SP in response to the ultrasonic energy generated by the ultrasonic transducer 52. In this embodiment, the third antinode 212C arranged adjacent to the distal blade end 38D defines an amplitude 214 of the standing wave 208 which corresponds to the retracted reference distance 204 which, as noted above, is half the reciprocation distance 206 defined as the teeth 42 at the distal blade end 38D reciprocate proximally and distally within the sagittal plane SP. Put differently, positioning an antinode of the standing wave 208 adjacent to the distal blade end 38D results in the largest reciprocation distance 206 in some embodiments. It will be appreciated that the standing wave 208 described above and depicted in FIG. 21 is exemplary and could define different quantities of nodes and antinodes.

In this way, the surgical systems 30 and surgical tools 32 described herein afford numerous advantages in connection with medical and/or surgical procedures which involve cutting, removing, or otherwise manipulation relatively hard tissue T, such as bone. Specifically, it will be appreciated that movement of the saw blade 36 in the superimposed first and second modes M1, M2 allows the teeth 42 of the saw blade 36 reciprocate proximally and distally within the sagittal plane SP a plurality of times during a single oscillation of the saw blade 36 back and forth about the pivot axis PA within the sagittal plane SP.

When compared to conventional sagittal saws, the surgical system 30 of the present disclosure is able to make more cuts over time which each remove a relatively small amount of tissue T, resulting in a smaller "chip size" during cutting, which promotes chip evacuation and helps prevent the accumulation of swarf between the teeth 42 of the saw blade 36. This, in turn, helps reduce the amount of friction and heat generated during cutting, which in some embodiments may promote improved durability of the teeth 42 and thereby increase the useful life of the saw blade 36. Furthermore, because the cuts made to the tissue T are relatively small, reactive forces which act on the teeth 42 as tissue T is cut are correspondingly small. Here, smaller reactive forces acting on the teeth 42 results in a reduced tendency for the saw blade 36 to "skive and dive" off the sagittal plane SP during use which, in turn, allows the surgeon the handle the surgical tool 32 with improved control and thereby cut tissue T in a predictable manner in connection with a number of different types of medical and surgical procedures. Additionally, an occurrence of vibrational motion of the distal blade end 38D of the saw blade 36 out of the sagittal plane SP (i.e., normal to the sagittal plane SP) may be advantageous when cutting bone, as it may allow the teeth 42 to create a slightly wider kerf, yielding extra clearance for the body 38 of the blade 36 to enter the kerf and to thus reduce a friction surface contact between the blade body 38 and the bone, resulting in less dissipation of energy by friction.

In the drawings, the same reference numbers indicate the same elements. Further, some or all of these elements could be changed. With regard to the media, processes, systems, methods, heuristics, etc. described herein, it should be understood that, although the steps of such processes, etc. have been described as occurring according to a certain ordered sequence, such processes could be practiced with the described steps performed in an order other than the order described herein. It further should be understood that certain steps could be performed simultaneously, that other steps could be added, or that certain steps described herein could be omitted. In other words, the descriptions of processes herein are provided for the purpose of illustrating certain embodiments, and should in no way be construed so as to limit the claims.

Accordingly, it is to be understood that the above description is intended to be illustrative and not restrictive. Many embodiments and applications other than the examples provided would be apparent upon reading the above description. The scope should be determined, not with reference to the above description, but should instead be determined with reference to the appended claims, along with the full scope of equivalents to which such claims are entitled. It is anticipated and intended that future developments will occur in the technologies discussed herein, and that the disclosed systems and methods will be incorporated into such future embodiments. In sum, it should be understood that the application is capable of modification and variation.

All terms used in the claims are intended to be given their ordinary meanings as understood by those knowledgeable in the technologies described herein unless an explicit indication to the contrary is made herein. In particular, use of the singular articles such as "a," "the," "said," etc. should be read to recite one or more of the indicated elements unless a claim recites an explicit limitation to the contrary.

It will be further appreciated that the terms "include," "includes," and "including" have the same meaning as the terms "comprise," "comprises," and "comprising." Moreover, it will be appreciated that terms such as "first," "second," "third," and the like are used herein to differentiate certain structural features and components for the non-limiting, illustrative purposes of clarity and consistency.

As used herein, the adverb "substantially" means that a shape, structure, measurement, quantity, time, etc. may deviate from an exact described geometry, distance, measurement, quantity, time, etc., because of imperfections in materials, machining, manufacturing, transmission of data, computational speed, etc.

The Abstract is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separately claimed subject matter.

Several embodiments have been discussed in the foregoing description. However, the embodiments discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

The invention claimed is:

1. A surgical tool for use in moving a saw blade in a sagittal plane, the saw blade having a distal blade end with teeth, said surgical tool comprising:
   a handpiece body;
   a carrier operatively attached to said handpiece body, said carrier configured for oscillating movement about a pivot axis;
   a retainer operatively attached to said carrier for concurrent oscillating movement about said pivot axis, said retainer configured to releasably secure the saw blade in the sagittal plane relative to said handpiece body;
   an actuator coupled to said handpiece body, said actuator configured to selectively oscillate said carrier relative to said handpiece body such that said retainer and the saw blade pivot back and forth about said pivot axis within the sagittal plane; and
   an ultrasonic transducer operatively attached to said handpiece body, said ultrasonic transducer configured to selectively generate ultrasonic energy to resonate the saw blade such that the teeth at the distal blade end reciprocate proximally and distally within the sagittal plane.

2. The surgical tool as set forth in claim 1, further comprising a waveguide body interposed in force-translating relation between said retainer and said ultrasonic transducer to direct ultrasonic energy generated by said ultrasonic transducer toward said retainer.

3. The surgical tool as set forth in claim 2, wherein said waveguide body comprises:
   a mount portion to secure said ultrasonic transducer to said waveguide body, and
   a flange portion arranged between said retainer and said mount portion, with said flange portion operatively attached to said carrier such that said waveguide body and said carrier oscillate concurrently.

4. The surgical tool as set forth in claim 3, wherein said carrier comprises:
   a pivot housing defining a pivot axis and operatively attached to said flange portion of said waveguide body, and
   a pivot shaft coupled to said pivot housing for concurrent oscillating movement with said pivot housing.

5. The surgical tool as set forth in claim 4, wherein said flange portion of said waveguide body is arranged closer to said pivot axis than said mount portion of said waveguide body.

6. The surgical tool as set forth in claim 1, wherein:
   said actuator comprises a motor configured to selectively generate rotation torque about a motor axis and an output shaft with an eccentric head arranged for orbital motion about said motor axis;
   the surgical tool further comprises a linkage interposed between said motor and said carrier to translate rotation about said motor axis into oscillating movement about said pivot axis;
   said carrier further comprises a pivot shaft; and
   said linkage comprises a connecting rod interposed between said pivot shaft and said eccentric head to translate rotation of said output shaft about said motor axis into oscillating movement of said pivot shaft about said pivot axis.

7. The surgical tool as set forth in claim 1, further comprising a controller disposed in communication with said actuator and said ultrasonic transducer, said controller being configured to drive said actuator such that said carrier oscillates at an oscillating frequency, and said controller being further configured to drive said ultrasonic transducer such that ultrasonic energy is generated at a drive frequency which is greater than said oscillating frequency, wherein said drive frequency is one of:
   at least 50 times greater than said oscillating frequency;
   at least 150 times greater than said oscillating frequency; and
   between 18 kHz and 40 kHz.

8. The surgical tool as set forth in claim 7, further comprising an input control operatively attached to said handpiece body, arranged for engagement by a user, and disposed in communication with said controller; and
   wherein said controller is configured to communicate an actuator drive signal to said actuator in response to engagement of said input control by the user to facilitate driving said actuator, and to communicate a transducer drive signal to said ultrasonic transducer in response to engagement of said input control by the user to facilitate generating ultrasonic energy with said ultrasonic transducer.

9. A surgical system for use in cutting tissue in a sagittal plane, said surgical system comprising:
   a saw blade configured to engage tissue in the sagittal plane, said saw blade comprising a blade body extending between a proximal blade end and a distal blade end, a retention mount formed in said blade body adjacent to said proximal blade end, and teeth formed at said distal blade end to engage tissue within the sagittal plane; and
   a surgical tool to move said saw blade in the sagittal plane, said surgical tool comprising:
      a handpiece body,
      a carrier operatively attached to said handpiece body, said carrier configured for oscillating movement about a pivot axis,
      a retainer operatively attached to said carrier for concurrent oscillating movement about said pivot axis, said retainer configured to releasably engage said retention mount of said saw blade to secure said saw blade in the sagittal plane relative to said handpiece body,
      an actuator coupled to said handpiece body, said actuator configured to selectively oscillate said carrier relative to said handpiece body such that said retainer and said saw blade pivot back and forth about said pivot axis within the sagittal plane, and
      an ultrasonic transducer operatively attached to said handpiece body, said ultrasonic transducer configured to selectively generate ultrasonic energy to resonate said saw blade such that said teeth at said distal blade end reciprocate proximally and distally within the sagittal plane.

10. The surgical system as set forth in claim 9, wherein:
   said surgical tool further comprises a waveguide body interposed in force-translating relation between said retainer and said ultrasonic transducer to direct ultrasonic energy generated by said ultrasonic transducer toward said saw blade;
   said waveguide body comprises:
      a mount portion to secure said ultrasonic transducer to said waveguide body, and
      a flange portion arranged between said retainer and said mount portion, with said flange portion operatively attached to said carrier such that said waveguide body and said carrier oscillate concurrently;

said waveguide body and said saw blade resonate to define a standing wave in response to ultrasonic energy generated by said ultrasonic transducer; and said standing wave propagates toward said distal blade end of said saw blade such that said teeth at said distal blade end reciprocate proximally and distally within the sagittal plane.

11. The surgical system as set forth in claim 10, wherein an amplitude of said standing wave taken adjacent to said distal blade end of said saw blade corresponds to half of a reciprocation distance defined as said teeth at said distal blade end reciprocate proximally and distally within the sagittal plane.

12. The surgical system as set forth in claim 10, wherein said standing wave passes through the sagittal plane to define a node arranged adjacent to said flange portion of said waveguide body so as to at least partially inhibit ultrasonic energy from being transferred from said ultrasonic transducer into said handpiece body.

13. The surgical system as set forth in claim 10, wherein said standing wave passes through the sagittal plane to define one or more nodes arranged between said ultrasonic transducer and said teeth of said saw blade.

14. The surgical system as set forth in claim 10, wherein said standing wave defines at least one antinode arranged adjacent to said distal blade end of said saw blade to facilitate reciprocation of said teeth of said saw blade within the sagittal plane in response to ultrasonic energy generated by said ultrasonic transducer.

15. The surgical system as set forth in claim 14, wherein said antinode arranged adjacent to said distal blade end of said saw blade defines an amplitude of said standing wave which corresponds to half of a reciprocation distance defined as said teeth at said distal blade end reciprocate proximally and distally within the sagittal plane.

16. The surgical system as set forth in claim 9, wherein said ultrasonic transducer is coupled to said carrier for concurrent oscillating movement.

17. The surgical system as set forth in claim 9, wherein said ultrasonic transducer comprises a piezoelectric transducer.

\* \* \* \* \*